(12) United States Patent
Privitera et al.

(10) Patent No.: US 9,393,023 B2
(45) Date of Patent: Jul. 19, 2016

(54) APPARATUS AND METHODS FOR DEPLOYING A CLIP TO OCCLUDE AN ANATOMICAL STRUCTURE

(75) Inventors: Salvatore Privitera, Mason, OH (US); Livyn O. Okorocha, Cincinnati, OH (US)

(73) Assignee: AtriCure, Inc., Mason, OH (US)

( * ) Notice: Subject to any disclaimer, the term of this patent is extended or adjusted under 35 U.S.C. 154(b) by 1915 days.

(21) Appl. No.: 12/352,937

(22) Filed: Jan. 13, 2009

(65) Prior Publication Data
US 2010/0179570 A1 Jul. 15, 2010

(51) Int. Cl.
*A61B 17/10* (2006.01)
*A61B 17/122* (2006.01)

(52) U.S. Cl.
CPC ................... *A61B 17/122* (2013.01)

(58) Field of Classification Search
CPC ...................................... A61B 17/122
USPC ................................. 606/151, 142
See application file for complete search history.

(56) References Cited

U.S. PATENT DOCUMENTS

| | | | |
|---|---|---|---|
| 2,060,724 A | 11/1936 | Carroll | |
| 2,371,978 A | 3/1945 | Perham | |
| 3,032,039 A | 5/1962 | Beaty | |
| 3,496,932 A | 2/1970 | Prisk | |
| 3,682,180 A | 8/1972 | McFarlane | |
| 3,818,784 A * | 6/1974 | McClure | 294/99.2 |
| 3,854,482 A | 12/1974 | Laugherty et al. | |
| 3,856,016 A | 12/1974 | Davis | |
| 3,856,017 A | 12/1974 | Perisse et al. | |
| 3,856,018 A | 12/1974 | Perisse et al. | |
| 3,954,108 A | 5/1976 | Davis | |
| 4,226,239 A | 10/1980 | Polk et al. | |
| 4,274,415 A | 6/1981 | Kanamoto et al. | |
| 4,493,319 A | 1/1985 | Polk et al. | |
| 4,552,128 A | 11/1985 | Haber | |
| 4,654,594 A | 3/1987 | Sepponen | |
| 4,788,966 A | 12/1988 | Yoon | |
| 4,791,707 A | 12/1988 | Tucker | |
| 4,865,037 A | 9/1989 | Chin et al. | |
| 4,869,268 A | 9/1989 | Yoon | |
| 4,917,677 A | 4/1990 | McCarthy | |
| 4,950,284 A | 8/1990 | Green et al. | |
| 4,991,578 A | 2/1991 | Cohen | |
| 5,007,426 A | 4/1991 | Le Roux | |
| 5,026,379 A | 6/1991 | Yoon | |

(Continued)

FOREIGN PATENT DOCUMENTS

| | | | |
|---|---|---|---|
| EP | 1 584 293 A1 | 10/2005 | |
| EP | 1 600 108 A2 | 11/2007 | |

(Continued)

OTHER PUBLICATIONS

Allen, et al., "Pericardial Effusion: Subxiphoid Pericardiostomy versus Percutaneous Catheter Drainage", The Annals of Thoracic Surg., Feb. 1999, vol. 67, No. 2, pp. 437-440.

(Continued)

*Primary Examiner* — Gergory Anderson
(74) *Attorney, Agent, or Firm* — Porter Wright Morris & Arthur LLP; Ryan Willis

(57) ABSTRACT

Apparatus and methods for deploying a clip to occlude an anatomical structure including a clip holder assembly that is an interface between the clip and a deployment device.

15 Claims, 14 Drawing Sheets

(56) References Cited

U.S. PATENT DOCUMENTS

| | | |
|---|---|---|
| 5,100,416 A | 3/1992 | Oh et al. |
| 5,108,420 A | 4/1992 | Marks |
| 5,119,804 A | 6/1992 | Anstadt |
| 5,171,250 A | 12/1992 | Yoon |
| 5,190,541 A | 3/1993 | Abele et al. |
| 5,217,030 A | 6/1993 | Yoon |
| 5,217,473 A | 6/1993 | Yoon |
| 5,258,000 A | 11/1993 | Gianturco |
| 5,282,811 A | 2/1994 | Booker et al. |
| 5,282,829 A | 2/1994 | Hermes |
| 5,282,844 A | 2/1994 | Stokes |
| 5,290,299 A | 3/1994 | Fain et al. |
| 5,306,234 A | 4/1994 | Johnson |
| 5,309,927 A | 5/1994 | Welch |
| 5,334,209 A | 8/1994 | Yoon |
| 5,336,252 A | 8/1994 | Cohen |
| 5,342,373 A | 8/1994 | Stefanchik et al. |
| 5,366,459 A | 11/1994 | Yoon |
| 5,403,311 A | 4/1995 | Abele et al. |
| 5,403,343 A | 4/1995 | Sugarbaker |
| 5,425,740 A | 6/1995 | Hutchinson, Jr. |
| 5,439,156 A | 8/1995 | Grant et al. |
| 5,445,167 A | 8/1995 | Yoon et al. |
| 5,452,733 A | 9/1995 | Sterman et al. |
| 5,549,628 A | 8/1996 | Cooper et al. |
| 5,575,795 A | 11/1996 | Anderson |
| 5,582,616 A | 12/1996 | Bolduc et al. |
| 5,609,599 A | 3/1997 | Levin |
| 5,620,452 A | 4/1997 | Yoon |
| 5,643,255 A | 7/1997 | Organ |
| 5,643,291 A | 7/1997 | Pier et al. |
| 5,665,100 A | 9/1997 | Yoon |
| 5,667,518 A | 9/1997 | Pannell |
| 5,676,636 A | 10/1997 | Chin |
| 5,681,330 A | 10/1997 | Hughett et al. |
| 5,681,349 A | 10/1997 | Sugarbaker |
| 5,683,405 A | 11/1997 | Yacoubian et al. |
| 5,695,505 A | 12/1997 | Yoon |
| 5,702,411 A | 12/1997 | Back et al. |
| 5,709,224 A | 1/1998 | Behl et al. |
| 5,727,569 A | 3/1998 | Benetti et al. |
| 5,728,121 A | 3/1998 | Bimbo et al. |
| 5,735,848 A | 4/1998 | Yates et al. |
| 5,758,420 A | 6/1998 | Schmidt et al. |
| 5,766,217 A | 6/1998 | Christy |
| 5,782,397 A | 7/1998 | Koukline |
| 5,782,844 A | 7/1998 | Yoon et al. |
| 5,797,960 A | 8/1998 | Stevens et al. |
| 5,810,851 A | 9/1998 | Yoon |
| 5,810,882 A | 9/1998 | Bolduc et al. |
| 5,823,956 A | 10/1998 | Roth et al. |
| 5,824,008 A | 10/1998 | Bolduc et al. |
| 5,827,216 A | 10/1998 | Igo et al. |
| 5,827,306 A | 10/1998 | Yoon |
| 5,830,221 A | 11/1998 | Stein et al. |
| 5,833,700 A | 11/1998 | Fogelberg et al. |
| 5,843,121 A | 12/1998 | Yoon |
| 5,843,152 A | 12/1998 | Tu et al. |
| 5,849,019 A | 12/1998 | Yoon |
| 5,865,791 A | 2/1999 | Whayne et al. |
| 5,891,162 A | 4/1999 | Sugarbaker et al. |
| 5,893,863 A | 4/1999 | Yoon |
| 5,919,202 A | 7/1999 | Yoon |
| 5,921,997 A | 7/1999 | Fogelberg et al. |
| 5,922,001 A | 7/1999 | Yoon |
| 5,922,002 A | 7/1999 | Yoon |
| 5,964,772 A | 10/1999 | Bolduc et al. |
| 5,984,917 A | 11/1999 | Fleischman et al. |
| 5,984,938 A | 11/1999 | Yoon |
| 5,984,939 A | 11/1999 | Yoon |
| 6,016,452 A | 1/2000 | Kasevich |
| 6,019,722 A | 2/2000 | Spence et al. |
| 6,042,563 A | 3/2000 | Morejohn et al. |
| 6,074,418 A | 6/2000 | Buchanan et al. |
| 6,077,261 A | 6/2000 | Behl et al. |
| 6,080,173 A | 6/2000 | Williamson |
| 6,088,889 A | 7/2000 | Luther et al. |
| 6,096,052 A | 8/2000 | Callister et al. |
| 6,099,550 A | 8/2000 | Yoon |
| 6,152,144 A | 11/2000 | Lesh et al. |
| 6,152,936 A | 11/2000 | Christy et al. |
| 6,161,543 A | 12/2000 | Cox et al. |
| 6,165,183 A | 12/2000 | Kuehn et al. |
| 6,203,541 B1 | 3/2001 | Keppel |
| 6,231,561 B1 | 5/2001 | Frazier et al. |
| 6,237,605 B1 | 5/2001 | Vaska et al. |
| 6,241,727 B1 | 6/2001 | Tu et al. |
| 6,248,124 B1 | 6/2001 | Pedros et al. |
| 6,258,105 B1 | 7/2001 | Hart et al. |
| 6,270,516 B1 | 8/2001 | Tanner et al. |
| 6,277,065 B1 | 8/2001 | Donofrio |
| 6,280,415 B1 | 8/2001 | Johnson |
| 6,290,674 B1 | 9/2001 | Roue et al. |
| 6,296,656 B1 | 10/2001 | Bolduc et al. |
| 6,299,612 B1 | 10/2001 | Ouchi |
| 6,312,447 B1 | 11/2001 | Grimes |
| 6,315,715 B1 | 11/2001 | Taylor et al. |
| 6,322,494 B1 | 11/2001 | Bullivant et al. |
| 6,328,688 B1 | 12/2001 | Borst et al. |
| 6,330,964 B1 | 12/2001 | Kayan et al. |
| 6,334,843 B1 | 1/2002 | Borst et al. |
| 6,336,898 B1 | 1/2002 | Borst et al. |
| 6,340,344 B1 | 1/2002 | Christopher |
| 6,357,100 B2 | 3/2002 | Speller, Jr. et al. |
| 6,387,105 B1 | 5/2002 | Gifford, III et al. |
| 6,402,765 B1 | 6/2002 | Monassevitch et al. |
| 6,416,554 B1 | 7/2002 | Alferness et al. |
| 6,428,548 B1 | 8/2002 | Durgin et al. |
| 6,436,088 B2 | 8/2002 | Frazier et al. |
| 6,447,542 B1 | 9/2002 | Weadock |
| 6,450,391 B1 | 9/2002 | Kayan et al. |
| 6,464,700 B1 | 10/2002 | Koblish et al. |
| 6,485,407 B2 | 11/2002 | Alferness et al. |
| 6,488,689 B1 | 12/2002 | Kaplan et al. |
| 6,491,701 B2 | 12/2002 | Tierney et al. |
| 6,491,706 B1 | 12/2002 | Alferness et al. |
| 6,494,211 B1 | 12/2002 | Boyd et al. |
| 6,506,149 B2 | 1/2003 | Peng et al. |
| 6,508,829 B1 | 1/2003 | Levinson et al. |
| 6,514,265 B2 | 2/2003 | Ho et al. |
| 6,520,974 B2 | 2/2003 | Tanner et al. |
| 6,562,051 B1 | 5/2003 | Bolduc et al. |
| 6,578,585 B1 | 6/2003 | Stachowski et al. |
| 6,579,304 B1 | 6/2003 | Hart et al. |
| 6,607,504 B2 | 8/2003 | Haarala et al. |
| 6,607,542 B1 | 8/2003 | Wild |
| 6,610,074 B2 | 8/2003 | Santilli |
| 6,645,196 B1 | 11/2003 | Nixon et al. |
| 6,652,515 B1 | 11/2003 | Maguire et al. |
| 6,666,861 B1 | 12/2003 | Grabek |
| 6,679,268 B2 | 1/2004 | Stevens et al. |
| 6,701,929 B2 | 3/2004 | Hussein |
| 6,709,442 B2 | 3/2004 | Miller et al. |
| 6,712,804 B2 | 3/2004 | Roue et al. |
| 6,719,767 B1 | 4/2004 | Kimblad |
| 6,746,461 B2 | 6/2004 | Fry |
| 6,770,081 B1 | 8/2004 | Cooper et al. |
| 6,793,664 B2 | 9/2004 | Mazzocchi et al. |
| 6,800,081 B2 | 10/2004 | Parodi |
| 6,849,075 B2 | 2/2005 | Bertolero et al. |
| 6,849,078 B2 | 2/2005 | Durgin et al. |
| 6,855,144 B2 | 2/2005 | Lesh |
| 6,869,431 B2 | 3/2005 | Maguire et al. |
| 6,875,224 B2 | 4/2005 | Grimes |
| 6,889,694 B2 | 5/2005 | Hooven |
| 6,896,684 B2 | 5/2005 | Monassevitch et al. |
| 6,911,032 B2 | 6/2005 | Jugenheimer et al. |
| 6,955,175 B2 | 10/2005 | Stevens et al. |
| 6,955,643 B2 | 10/2005 | Gellman et al. |
| 6,960,218 B2 | 11/2005 | Rennich |
| 6,981,628 B2 | 1/2006 | Wales |
| 7,011,669 B2 | 3/2006 | Kimblad |
| 7,033,378 B2 | 4/2006 | Smith et al. |
| 7,044,134 B2 | 5/2006 | Khairkhahan et al. |

(56) References Cited

U.S. PATENT DOCUMENTS

| | | | |
|---|---|---|---|
| 7,056,294 B2 | 6/2006 | Khairkhahan et al. | |
| 7,077,851 B2 | 7/2006 | Lutze et al. | |
| 7,113,831 B2 | 9/2006 | Hooven | |
| 7,118,582 B1 | 10/2006 | Wang et al. | |
| 7,169,164 B2 | 1/2007 | Borillo et al. | |
| 7,209,783 B2 | 4/2007 | Fellows et al. | |
| 7,226,458 B2 | 6/2007 | Kaplan et al. | |
| 7,318,829 B2 | 1/2008 | Kaplan et al. | |
| 7,424,965 B2 | 9/2008 | Racenet et al. | |
| 7,473,261 B2 | 1/2009 | Rennich | |
| 7,527,634 B2 | 5/2009 | Zenati et al. | |
| 7,644,848 B2 | 1/2010 | Swayze et al. | |
| 7,645,285 B2 * | 1/2010 | Cosgrove et al. | 606/151 |
| 7,896,895 B2 | 3/2011 | Boudreaux et al. | |
| 2001/0005787 A1 | 6/2001 | Oz et al. | |
| 2001/0039419 A1 | 11/2001 | Francinschelli et al. | |
| 2001/0039434 A1 | 11/2001 | Frazier et al. | |
| 2001/0039435 A1 | 11/2001 | Roue et al. | |
| 2002/0013605 A1 | 1/2002 | Bolduc et al. | |
| 2002/0022860 A1 | 2/2002 | Borillo et al. | |
| 2002/0026214 A1 | 2/2002 | Tanner et al. | |
| 2002/0026216 A1 | 2/2002 | Grimes | |
| 2002/0032454 A1 | 3/2002 | Durgin et al. | |
| 2002/0035374 A1 | 3/2002 | Borillo et al. | |
| 2002/0049457 A1 | 4/2002 | Kaplan et al. | |
| 2002/0055750 A1 | 5/2002 | Durgin et al. | |
| 2002/0058967 A1 | 5/2002 | Jervis | |
| 2002/0062130 A1 | 5/2002 | Jugenheimer et al. | |
| 2002/0065524 A1 | 5/2002 | Miller et al. | |
| 2002/0077660 A1 | 6/2002 | Kayan et al. | |
| 2002/0099390 A1 | 7/2002 | Kaplan et al. | |
| 2002/0103492 A1 | 8/2002 | Kaplan et al. | |
| 2002/0111637 A1 | 8/2002 | Kaplan et al. | |
| 2002/0111641 A1 | 8/2002 | Peterson et al. | |
| 2002/0143326 A1 | 10/2002 | Foley et al. | |
| 2002/0169377 A1 | 11/2002 | Khairkhahan et al. | |
| 2002/0177859 A1 | 11/2002 | Monassevitch et al. | |
| 2002/0177862 A1 | 11/2002 | Aranyi et al. | |
| 2003/0009441 A1 | 1/2003 | Holsten et al. | |
| 2003/0018362 A1 | 1/2003 | Fellows et al. | |
| 2003/0023248 A1 | 1/2003 | Parodi | |
| 2003/0023266 A1 | 1/2003 | Borillo et al. | |
| 2003/0055422 A1 | 3/2003 | Lesh | |
| 2003/0158464 A1 | 8/2003 | Bertolero | |
| 2004/0030335 A1 | 2/2004 | Zenati et al. | |
| 2004/0030355 A1 | 2/2004 | Schiller et al. | |
| 2004/0073241 A1 | 4/2004 | Barry et al. | |
| 2004/0097982 A1 | 5/2004 | Jugenheimer et al. | |
| 2004/0106937 A1 | 6/2004 | Berube et al. | |
| 2004/0215216 A1 | 10/2004 | Gannoe et al. | |
| 2005/0085808 A1 | 4/2005 | Nakao | |
| 2005/0149068 A1 | 7/2005 | Williams et al. | |
| 2005/0149069 A1 | 7/2005 | Bertolero et al. | |
| 2005/0203561 A1 | 9/2005 | Palmer et al. | |
| 2005/0277959 A1 | 12/2005 | Cosgrove et al. | |
| 2006/0020271 A1 | 1/2006 | Stewart et al. | |
| 2006/0084974 A1 | 4/2006 | Privitera et al. | |
| 2006/0161147 A1 | 7/2006 | Privitera et al. | |
| 2006/0161149 A1 | 7/2006 | Privitera et al. | |
| 2006/0212049 A1 | 9/2006 | Mohiuddin | |
| 2006/0253129 A1 | 11/2006 | Liddicoat et al. | |
| 2006/0271089 A1 | 11/2006 | Alejandro et al. | |
| 2007/0016228 A1 | 1/2007 | Salas | |
| 2007/0021761 A1 | 1/2007 | Phillips | |
| 2007/0027456 A1 | 2/2007 | Gartner et al. | |
| 2008/0033457 A1 | 2/2008 | Francischelli et al. | |
| 2009/0012545 A1 | 1/2009 | Williamson, IV et al. | |
| 2009/0069823 A1 | 3/2009 | Foerster et al. | |
| 2009/0253961 A1 | 10/2009 | Le et al. | |
| 2012/0035622 A1 | 2/2012 | Kiser et al. | |

FOREIGN PATENT DOCUMENTS

| | | |
|---|---|---|
| WO | WO 93/15791 | 8/1993 |
| WO | WO 98/18389 | 5/1998 |
| WO | WO 98/24378 | 6/1998 |
| WO | WO 98/24488 | 6/1998 |
| WO | WO 99/13785 | 3/1999 |
| WO | WO 99/13936 | 3/1999 |
| WO | WO 99/62409 | 12/1999 |
| WO | WO 99/62409 A1 | 12/1999 |
| WO | WO 01/35832 A2 | 5/2001 |
| WO | WO 01/97696 A1 | 12/2001 |
| WO | WO 03/011150 A1 | 2/2003 |
| WO | WO 03/096881 A2 | 11/2003 |
| WO | WO 2006/009729 A2 | 1/2006 |
| WO | WO 2007/009099 A2 | 1/2007 |
| WO | WO 2007/127664 A1 | 11/2007 |
| WO | PCT/US2006/027553 | 1/2008 |
| WO | PCT/US13/22600 | 4/2013 |

OTHER PUBLICATIONS

Beckman, et al., "Subxiphoid Approach for Implantable Cardioverter Defibrillator in Patients with Previous Coronary Bypass Surgery", PACE, Nov. 1992, vol. 15 Part I, pp. 1637-1638.

Coffin, L., "Use of the Surgical Stapler to Obliterate the Left Atrial Appendage", Surgery, Gynecology & Obstetrics, Jun. 1985, vol. 160, pp. 565-566.

Cox, et al., "Five-Year Experience with the Maze Procedure for Atrial Fibrillation", The Annals of Thoracic Surg., 1993, vol. 56, pp. 814-824.

DiSesa, et al., "Ligation of the Left Atrial Appendage Using an Automatic Surgical Stapler", Division of Cardiac Surgery, Brigham & Women's Hospital, Jul. 26, 1988, pp. 652-653.

Grewal, et al., "Evaluation of Subxiphoid Pericardial Window Used in the Detection of Occult Cardiac Injury", Injury, 1995, vol. 25, No. 5, pp. 305-310.

Habal, et al., "Simplified Subxiphoid Placement of Implantable Cardioverter Defibrillators Using a Posterior Rectus Pocket", The Annals of Thoracic Surg., 1994, vol. 57, pp. 723-725.

Hoit, et al., "Altered Left Atrial Compliance After Atrial Appendectomy, Influence on Left Atrial and Ventricular Filling", Circulation Research, 1993, vol. 72, pp. 167-175.

Johnson, et al., "The Left Atrial Appendage: Our most Lethal Human Attachment! Surgical Implications", European Journal of Cardio-Thoracic Surg, 2000, vol. 17, pp. 718-722.

Karagoz, et al., "Minimally Invasive Mitral Valve Surgery: The Subxiphoid Approach", The Annals of Thoracic Surg., 1999, vol. 67, pp. 1328-1333.

Krueger, et al., "Left Atrial Appendage Aneurysm: Correlation of Noninvasive with Clinical and Surgical Findings: Report of a Case", Circulation, 1975, vol. 52, pp. 732-738.

Kulik, et al., "Puncture of the Left Segments of the Heart and Aorta under Thoracoscopic Control in Diagnosis of Cardio-Vascular Diseases", Kardiologiia, 1974, vol. 14, No. 5, pp. 83-86, with English Abstract.

Landreneau, et al., "Video-Assisted Thoracic Surgery: Basic Technical Concepts and Intercostal Approach Strategies", The Annals of Thoracic Surg., 1992, vol. 54, pp. 800-807.

Landymore, et al., "Staple Closure of the Left Atrial Appendage", The Canadian Journal of Surgery, Mar. 1984, vol. 27, No. 2, pp. 144-145.

Landymore, et al., "Stapling of Left Atrial Appendage", The Annals of Thoracic Surg., 1989, vol. 47, p. 794.

Lindsay, B., "Obliteration of the Left Atrial Appendage: A Concept Worth Testing", The Annals of Thoracic Surg., 1996, vol. 61, p. 515.

Lipkin, et al., "Aneurysmal Dilation of Left Atrial Appendage Diagnosed by Cross Sectional Echocardiography and Surgically Removed", Heart Journal, 1985, vol. 53, pp. 69-71.

Lynch, et al., "Recanalization of the Left Atrial Appendage Demonstrated by Transesophageal Echocardiography", The Annals of Thoracic Surg., 1997, vol. 63, pp. 1774-1775.

(56) References Cited

OTHER PUBLICATIONS

Macris, et al., "Minimally Invasive Access of the Normal Pericardium: Initial Clinical Experience with a Novel Device", Clinical Cardiology, 1999, vol. 22 (Suppl I), pp. I-36-I-39).
Marrin, et al., "Subxiphoid Approach for Insertion of ICDs After Previous Median Sternotomy", The Annals of Thoracic Surg., 1993, vol. 56, pp. 312-315.
Mole, et al., "Desmoid Tumour in Thoracotomy Scar 5 Years After Excision of a Left Giant Atrial Appendage Aneurysm in Female with a Family History of Gardner's Syndrome", Thorac, Cardiovasc. Surgeon, 1992, vol. 40 pp. 300-302.
Omari, et al., "Effect of Right Atrial Appendectomy on the Release of Atrial Natriuretic Hormone", Journal of Thorac Cardiovasc. Surg., 1991, vol. 102, pp. 272-279.
Palatianos, et al., "Comparison of Effectiveness and Safety of Operations on the Pericardium", Chest, Jul. 1985, vol. 88 No. 1. pp. 30-33.
Robin, et al., "Strangulation of the Left Atrial Appendage through a Congenital Partial Pericardial Defect", Chest, Mar. 1975, vol. 67, No. 3, pp. 354-355.
Snow, et al., "Subxiphoid Pericardiotomy, A Safe, Accurate, Diagnostic and Therapeutic Approach to Pericardial and Intrapericardial Disease", The American Surgeon, May 1983, vol. 49, pp. 249-253.
Stewart, et al., "Sutureless Epicardial Pacemaker Lead: A Satisfactory Preliminary Experience", Chest, May 1975, vol. 67, No. 5, pp. 564-567.
Subramanian, V., "Clinical Experience with Minimally Invasive Reoperative Cornary ByPass Surgery", European Journal of Cardio-Thorac. Surg., 1996, vol. 10, pp. 1058-1063.
Subramanian, V., "Less invasive Arterial CABG on a Beating Heart", The Annals of Thoracic Surg., 1997, vol. 63, pp. S68-S71.
Subramanian, et al., "Minimally Invasive Direct Coronary Artery Bypass Grafting: Two-Year Clinical Experience", The Annals of Thoracic Surg., 1997, vol. 64, pp. 1648-1655.
Tabata, et al., "Role of Left Atrial Appendage in Left Atrial Reservoir Function as Evaluated by Left Atrial Appendage Clamping During Cardiac Surgery", American Journal Cardiol. , 1998, vol. 81, pp. 327-332.
Thomas, T., "Left Atrial Appendage and Valve Replacement", American Heart Journal, Dec. 1972, vol. 84, No. 6, pp. 838-839.
Wakabayashi, A., "Expanded Applications of Diagnostic and Therapeutic Thoracoscopy", Journal Thorac Cardiovasc. Surg., 1991, vol. 102, pp. 721-723.
Kuki, et al., "A Left Atrial Appendage Thrombus Without Mitral Stenosis—A Successful Case of Removal-", Journal of the Japanese Assoc. for Thoracic Surg., Mar. 1994, vol. 42, No. 3, pp. 385-388, with English Abstract.
Okawa, et al., "Eighty Cases of Minimally Invasive Direct Coronary Artery Bypass Grafting", The Japanese Journal of Thoracic Surgery, 1998, vol. 51, No. 4, with English Abstract.
Ganeshakrishnan, et al., "Congenital Intrapericardial Aneurysm of the Left-Atrial Appendage", Thorac, Cardiovasc. Surg. , 1992, vol. 40, pp. 382-384.
Aytac, et al., "Intrapericardial Aneurysm of the Left Atrial Appendix", Journal Cardiovasc. Surg., 1980, vol. 21, pp. 509-512.
Unknown, Endowrist Instruments and Accessories Catalog, Intuitive Surgical, Sunnyvale, California, Sep. 2005.
Kamohara et al, Impact of left atrial appendage exclusion on left atrial function, J Thorac Cardiov Surg 2007;133:174-81, © 2007 American Association for Thoracic Surgery, USA.
Fumoto et al, A novel device for left atrial appendage exclusion: The third-generation atrial exclusion device, J Thorac Cardiov Surg 2008;136:1019-27, © 2008 American Association for Thoracic Surgery, USA.
Lipkin et al, Aneurysmal dilation of left atrial appendage diagnosed by cross sectional echocardiography and surgically removed, Br Heart J 1985; 53:69-71, National Heart Hospital, London, UK.
Cohn et al, Right thoracotomy, femorofemoral bypass, and deep hypothermia for re-replacement of the mitral valve, Ann Thorac Surg 1989;48:69-71, © 1989 Society of Thoracic Surgeons, USA.
Al-Saady et al, Left atrial appendage: structure, function, and role in thrombo-boembolism, Heart 1999;82:547-555, St. George's Hosp Med School, London UK.
Kaymaz et al, Location, Size and Morphological Characteristics of Left Atrial Thrombi as Assessed by Echocardiography in Patients with Rheumatic Mitral Valve Disease, Eur. J Echocardiography, vol. 2, Issue 4, Dec. 2001, pp. 270-276, © 2001 The European Society of Cardiology.
Rosenzweig et al, Thromboembolus from a Ligated Left Atrial Appendage, J Am Soc Echocardiography, vol. 14, pp. 396-398, May 2001, © 2001 American Society of Echocardiography, USA.
Hondo et al, The Role of the Left Atrial Appendage; A Volume Loading Study in Open-chest Dogs, Jpn Heart J, Mar. 1995, pp. 225-234, Japan.
Veinot et al, Anatomy of the Normal Left Atrial Appendage: A Quantitative Study of Age-Related Changes . . . , ahajournals 1997; 96: 3112-3115, USA.
Halperin et al, Obliteration of the Left Atrial Appendage for Prevention of Thromboembolis, J Am Coll of Cardiol, 2003;42:1259-1261, USA.
Unknown, Transesophageal Echocardiographic Correlates of Thromboembolism in High Risk Patients with Nonvalvular Atrial Fibrillation, The American College of Physicians, Apr. 1998, pp. 639-647, © 1998 American College of Physicians, USA.
Omari et al, Effect of right atrial appendectomy on the release of atrial natriuretic hormone, J Thorac Cardiovasc Surg 1991; 102:272-279, USA.
Mole et al, Desmoid Tumour in Thoractomy Scar 5 Years After Excision of a Left Giant Atrial Appendage Aneurysm in Female with a Family History of Gardner's Syndrome, Thorac Cardiovasc Surg 40 (1991) pp. 300-302, © 1992 George Thieme Verlag Stuttgart, New York.
Crystal et al, Left Atrial Appendage Occlusion Study (LAA0S): A randomized clinical trial of left atrial appendage occlusion during routine coronary artery bypass graft surgery for long-term stroke prevention; Am Heart J 2003; 145:174-178, © 2003 Mosby, Inc., USA.
Garcia-Fernadez et al, Role of left atrial appendage obliteration in stroke reduction in patients with mitral valve prosthesis: A transeophageal echocardiographic study, J Am Coll Cardiol 2003;42:1253-1258, © 2003 American College of Cardiology Foundation, USA.
Burke et al, Improved Surgical Approach to Left Atrial Appendage Aneurysm, J Cardi Surg, 1992, vol. 7, No. 2, pp. 104-107, USA.
Fisher et al, Large Gradient Across a Partially Ligated Left Atrial Appendage, J Am Soc Echocardiography, vol. 11, No. 12, pp. 1163-1165, © 1998 American Society of Echocardiography, USA.
Grundeman et al, Experimental videothoracoscopic cannulation of the left atrial appendix, Surg Endosc (1993) 7:511-513, © 1993 Springer-Verlag New York, Inc., USA.

* cited by examiner

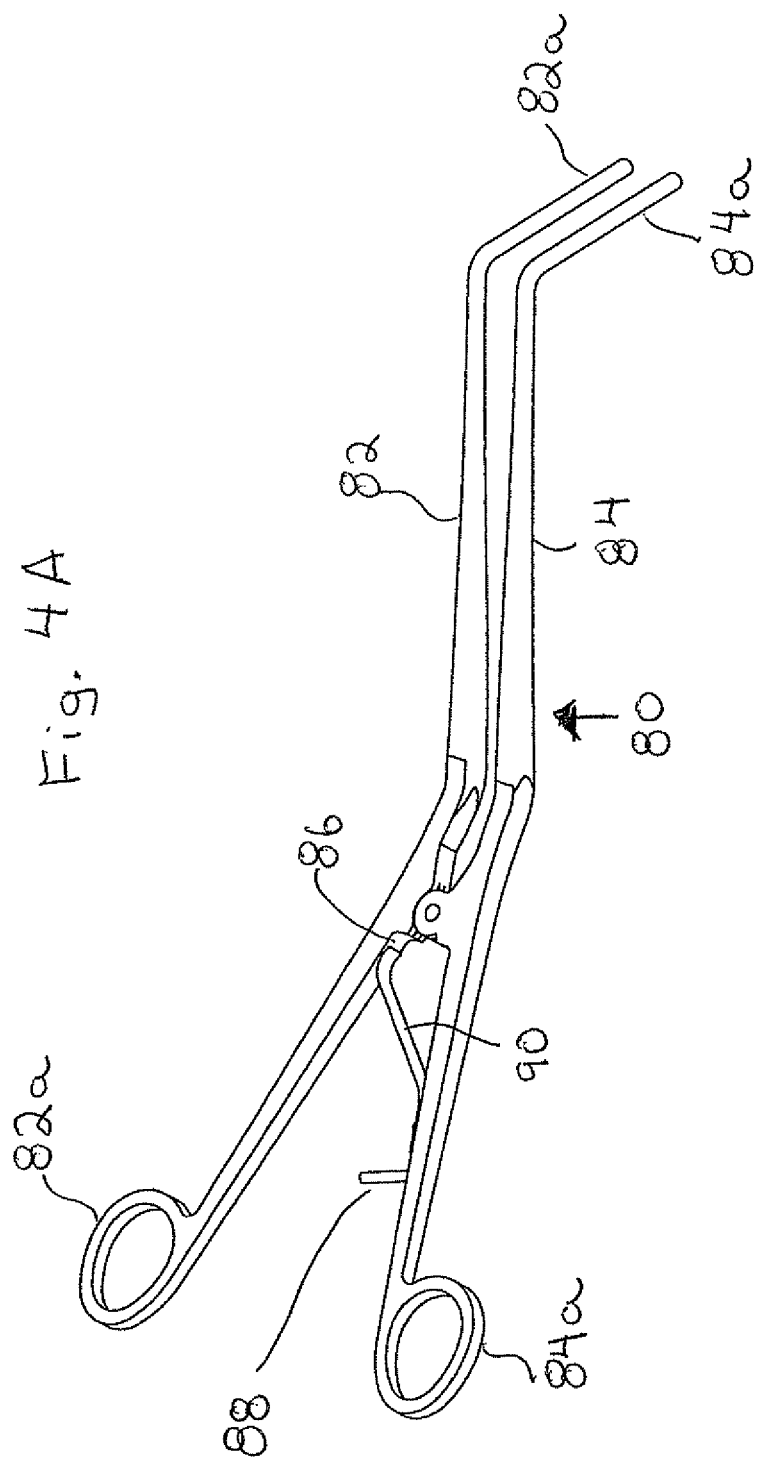

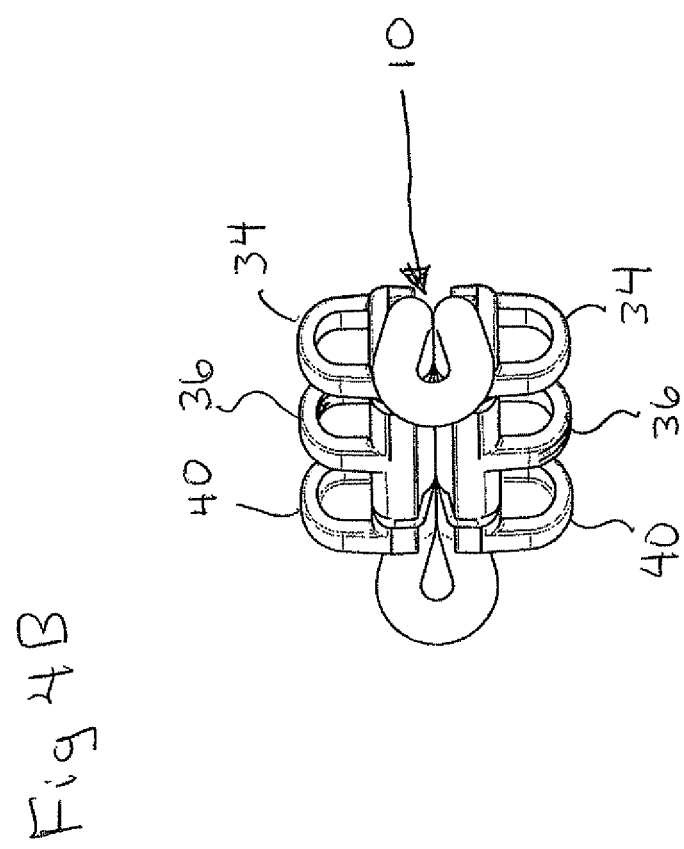

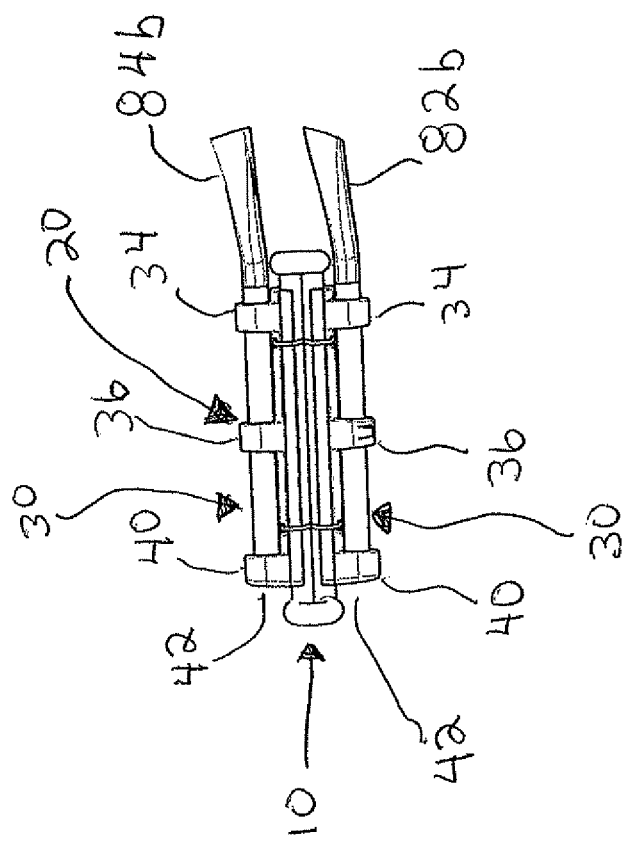

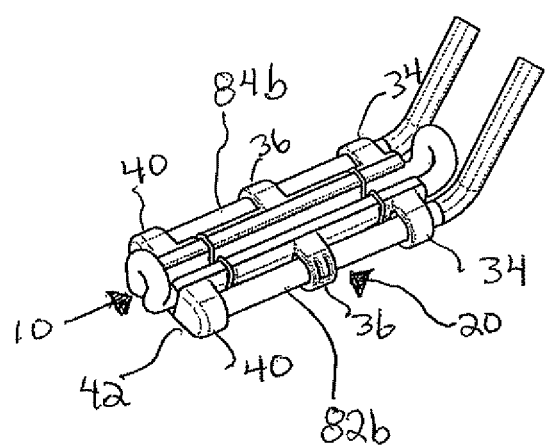

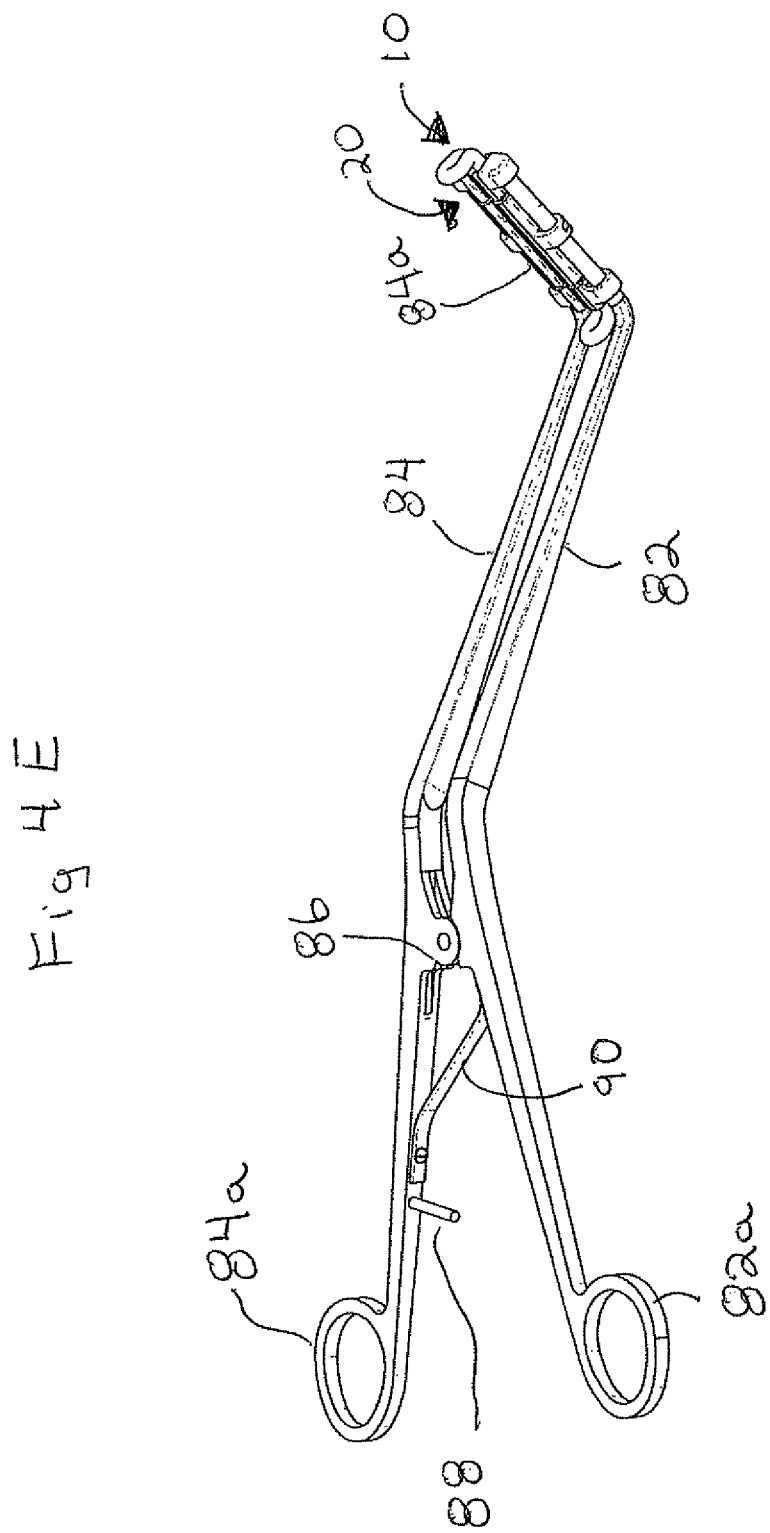

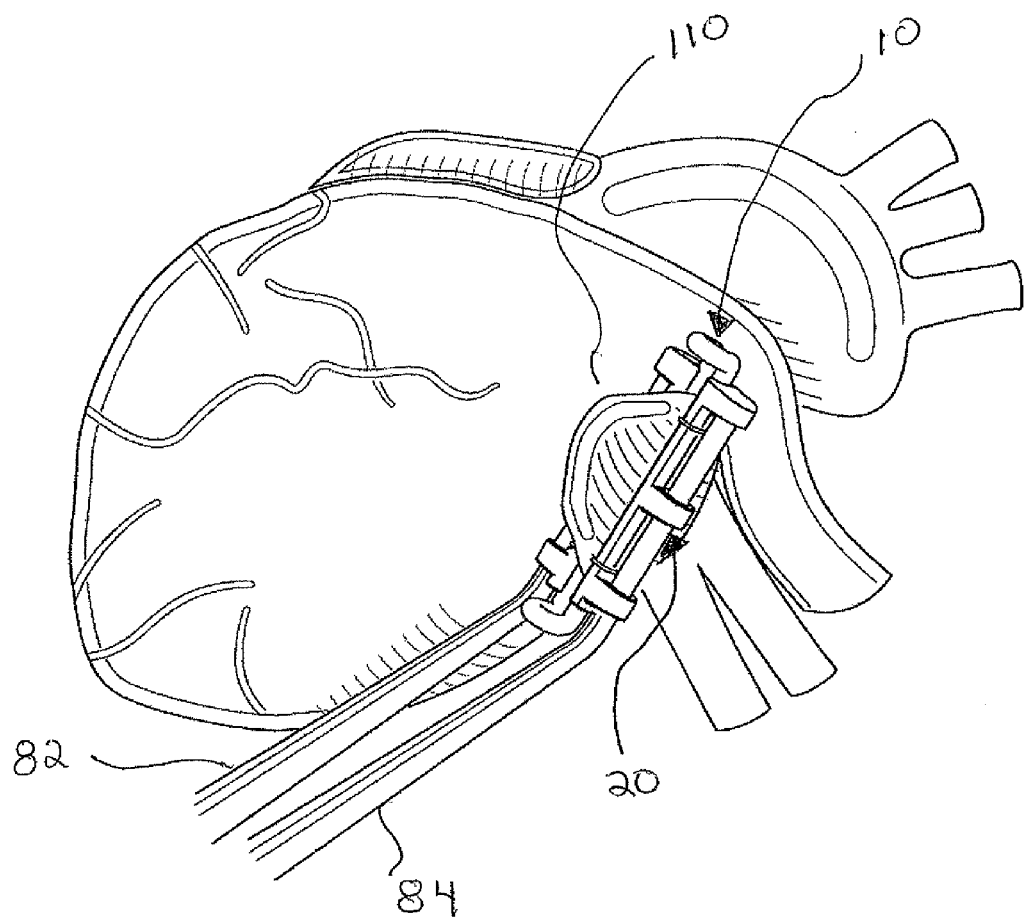

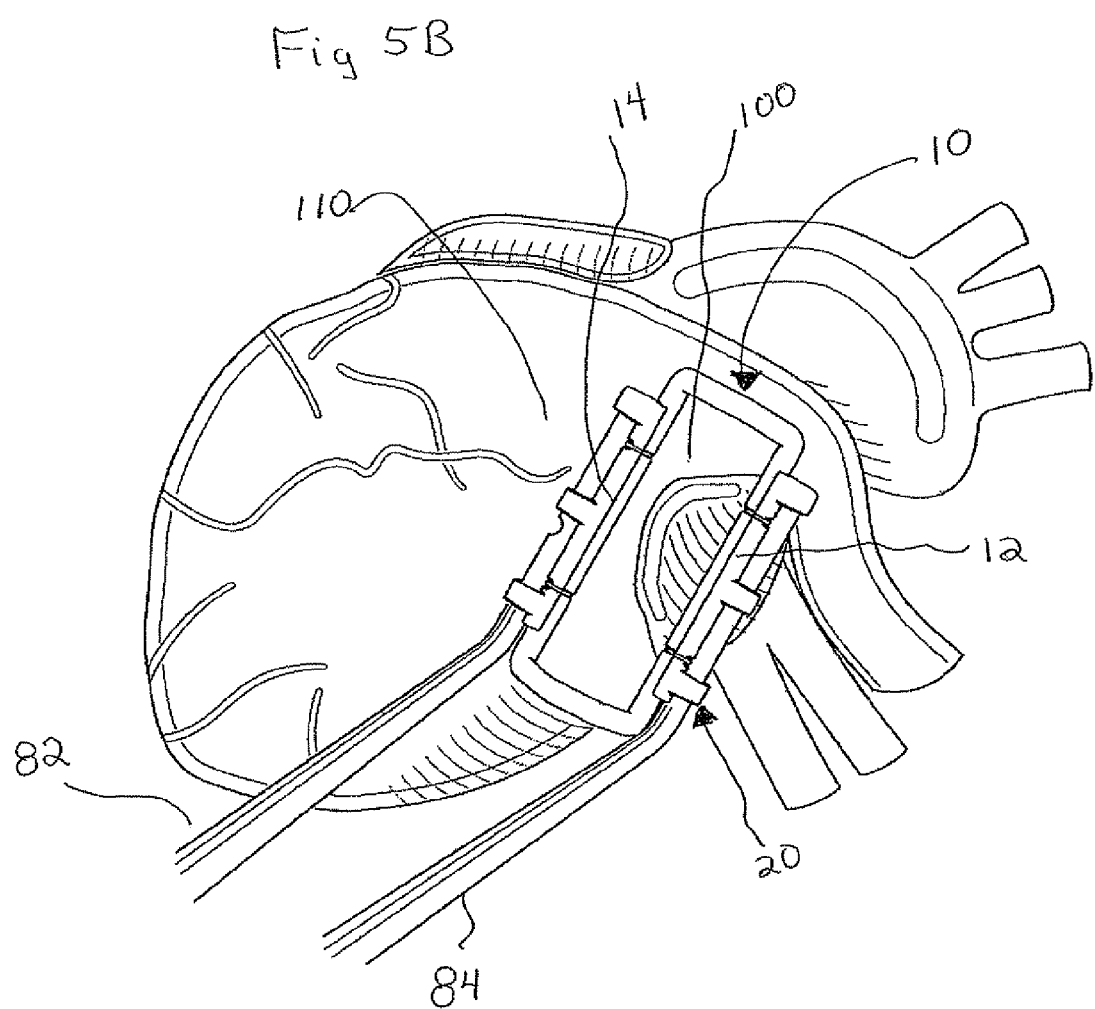

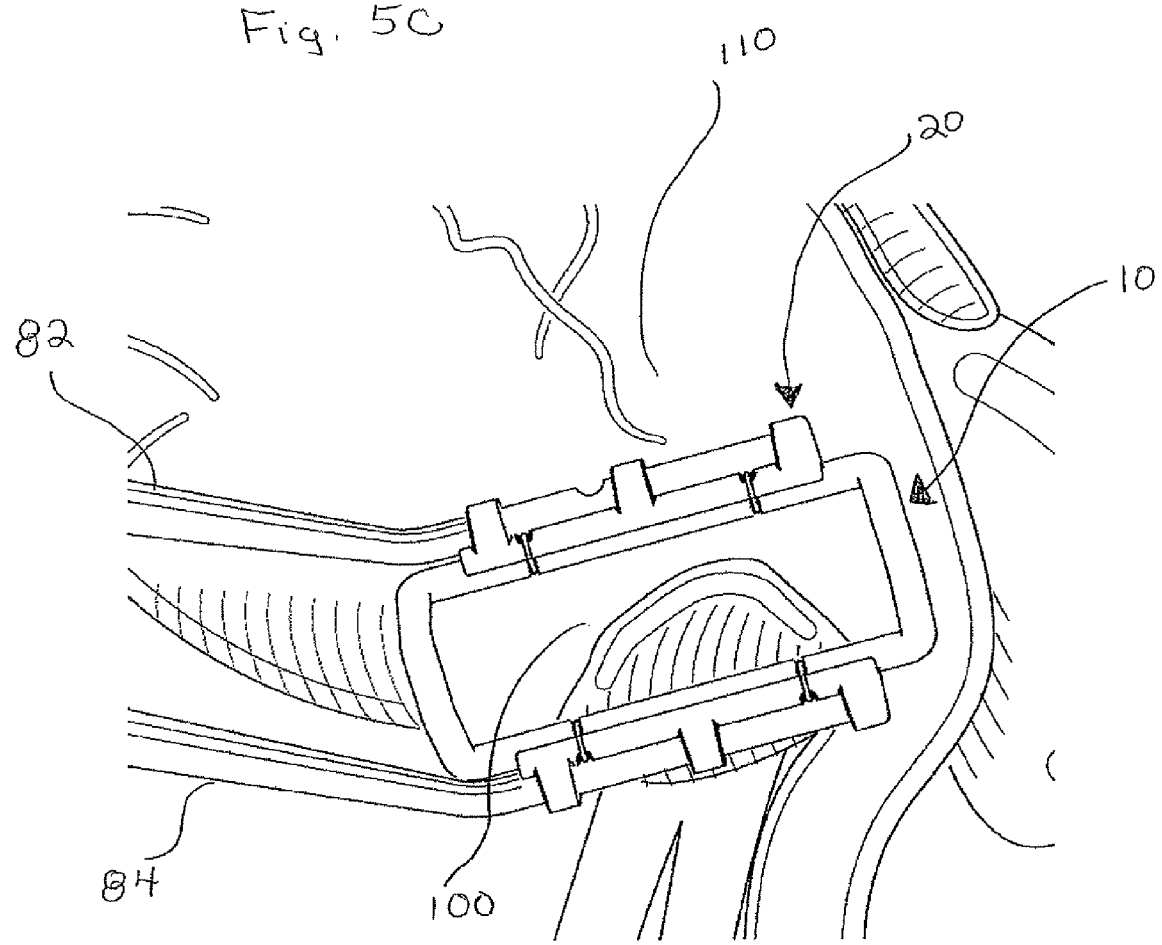

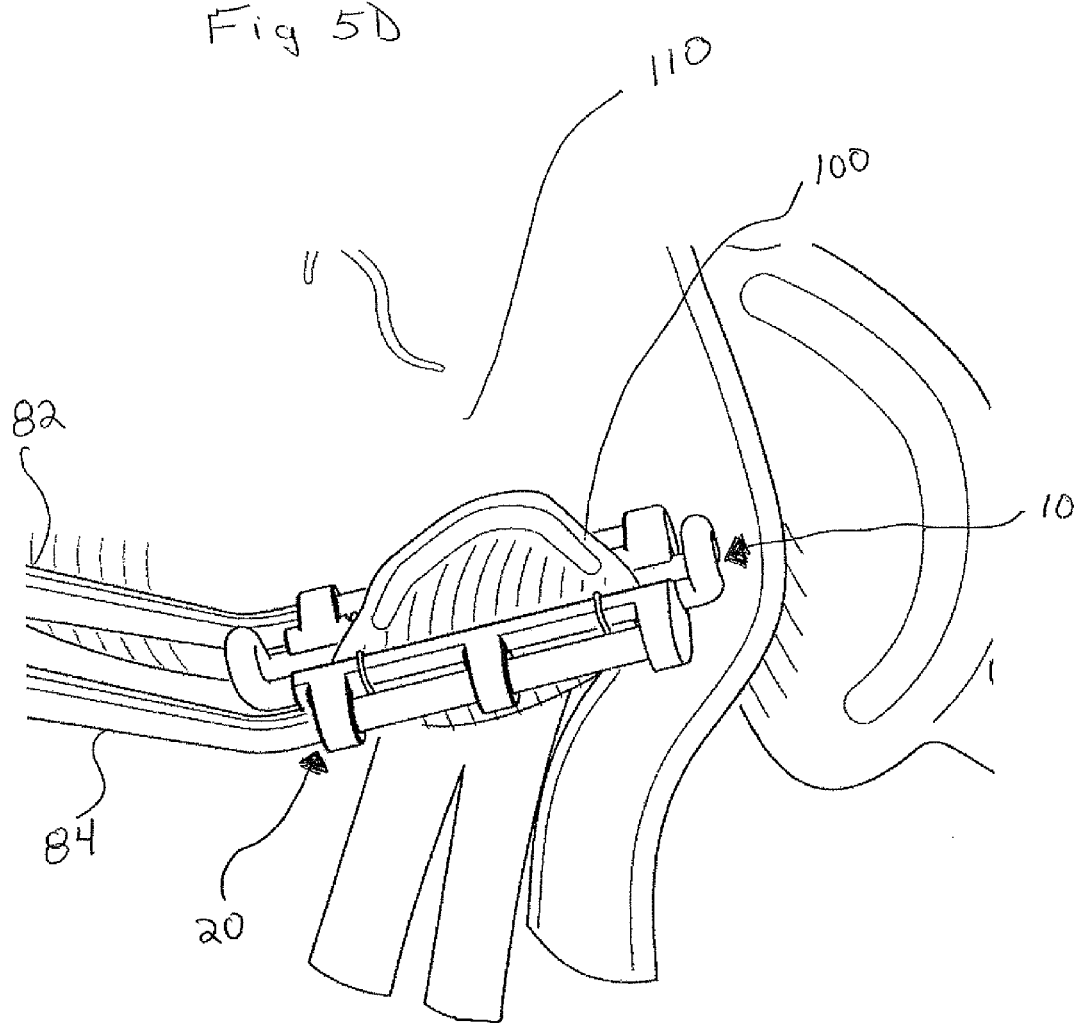

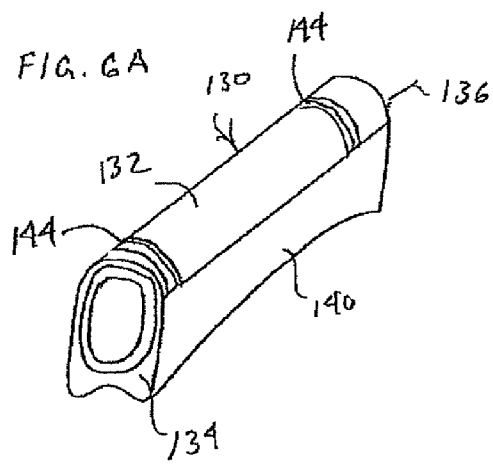
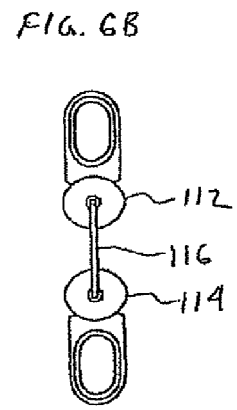
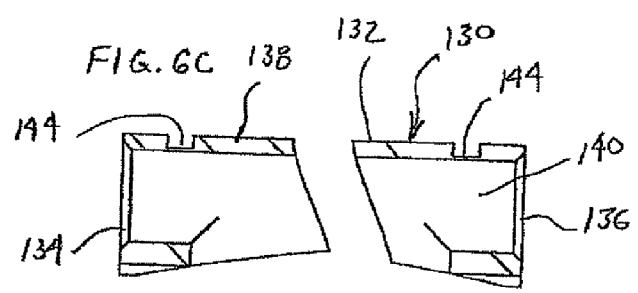
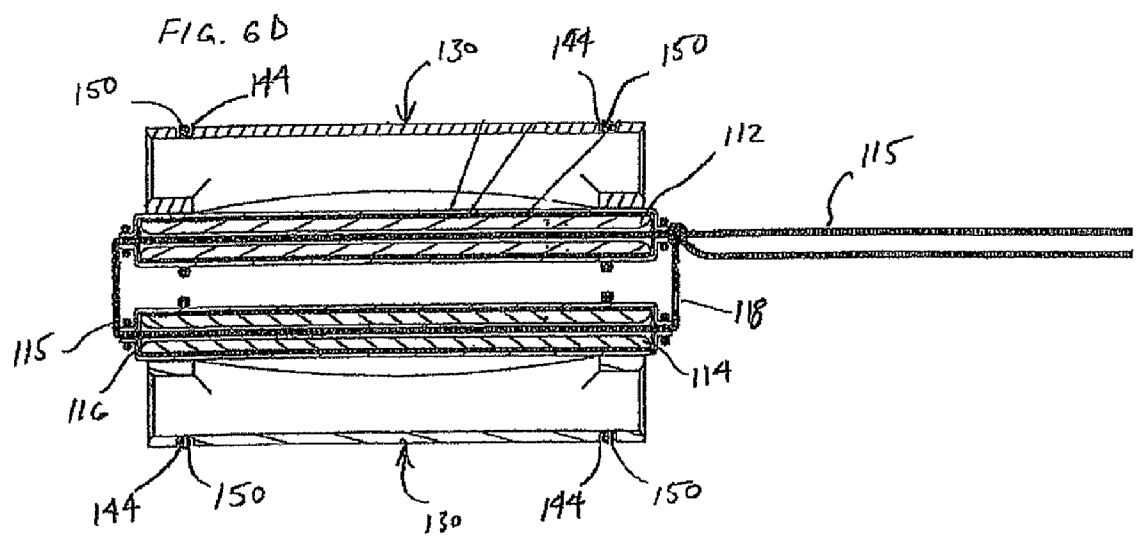

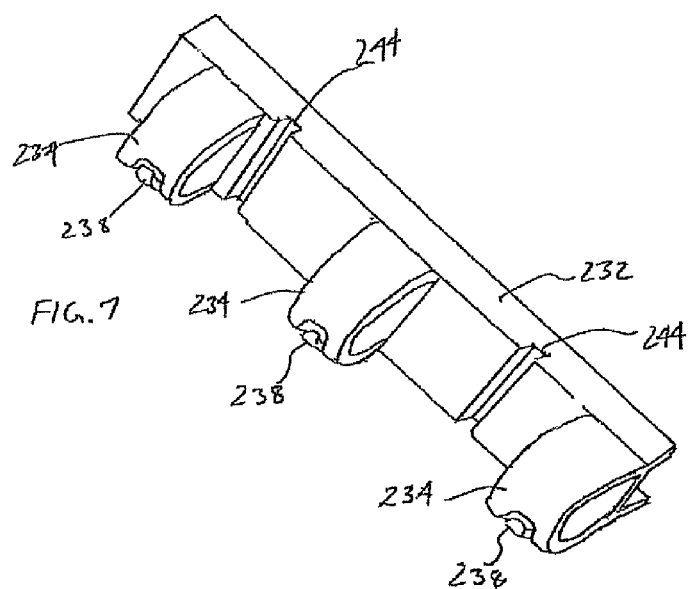
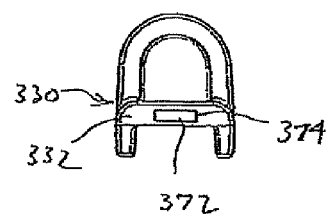
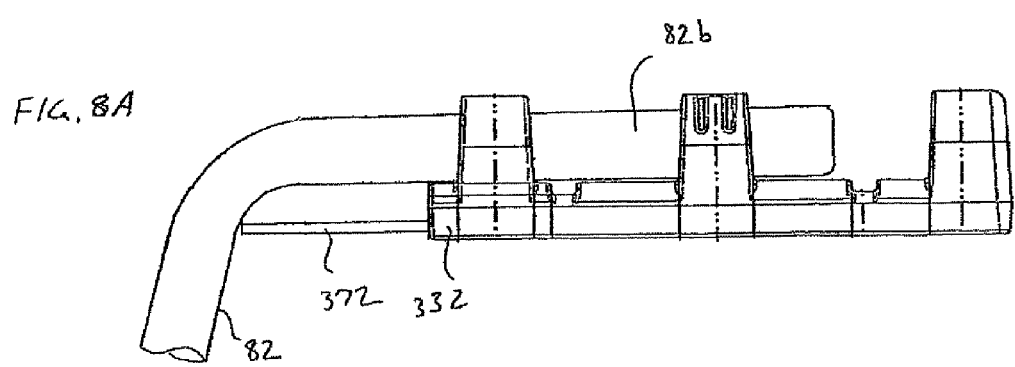
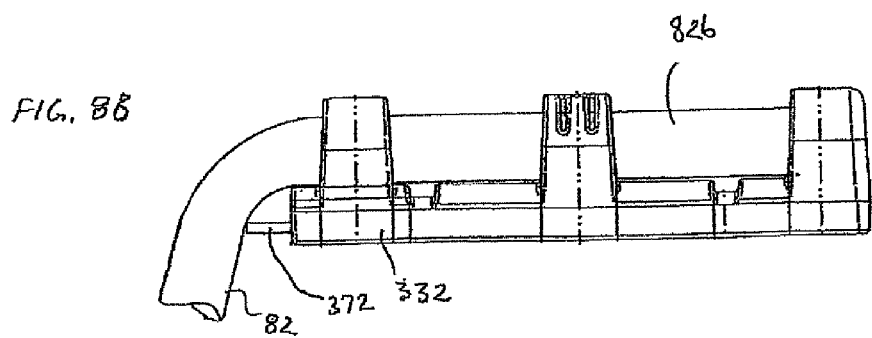

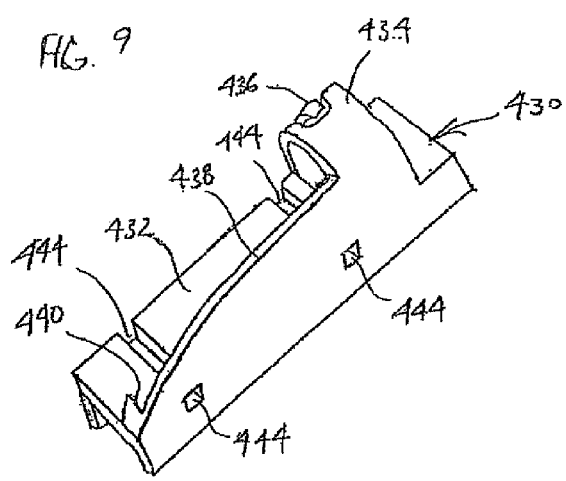
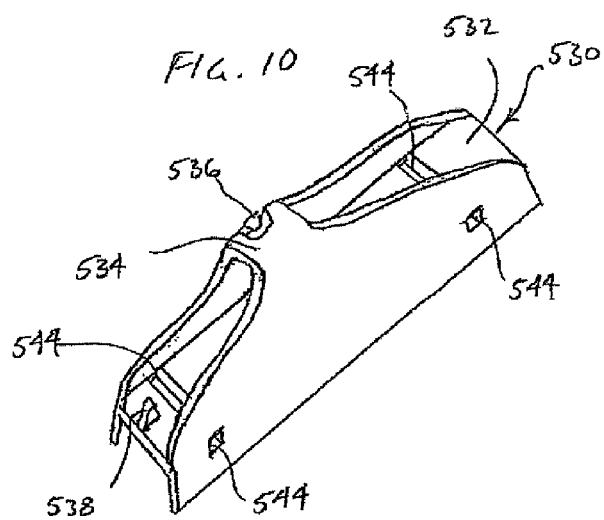
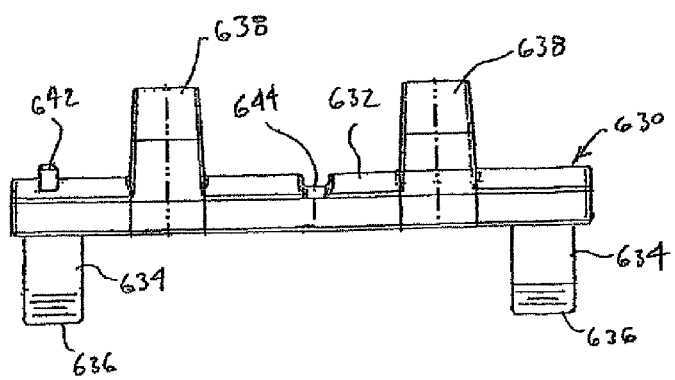
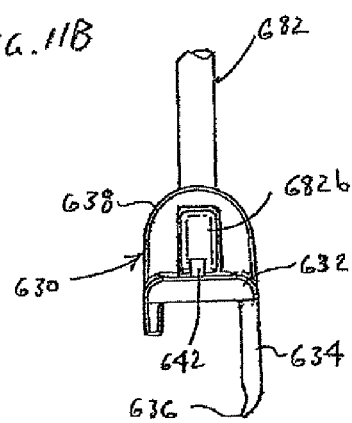

APPARATUS AND METHODS FOR DEPLOYING A CLIP TO OCCLUDE AN ANATOMICAL STRUCTURE

BACKGROUND

This disclosure relates generally to apparatus and methods that may be used to occlude an anatomical structure, and more particularly to apparatus and methods for deploying an occlusion clip. It may be desirable to occlude an anatomical structure such as, for example, the left atrial appendage (LAA). It will be appreciated that blood may otherwise tend to clot in a non-occluded LAA, which may increase the risk of stroke. Occlusion of the LAA may prevent blood from entering the LAA, thereby preventing blood from clotting in the LAA. Such occlusion may therefore also prevent blood clots from exiting the LAA into the blood stream, such that the risk of stroke may be reduced.

Of course, there may be other purposes for occluding the LAA, and there are a variety of other anatomical structures that may be occluded. Due to the varying dimensions of the LAA and other anatomical structures between individuals, it will be appreciated that it may be desirable to provide occlusion devices of varying dimensions and/or configurations to correspond to the particular anatomical structure intended to be occluded or for other purposes. While a variety of techniques and devices have been used to treat anatomical structures such as the LAA, it is believed that no one prior to the inventors has previously made or used an apparatus or methods as described herein.

SUMMARY

The present disclosure generally presents apparatus and methods for deploying a clip to occlude anatomical structures. In a first aspect, a clip holder assembly for use in deploying a clip adapted to occlude an anatomical structure is presented wherein the clip includes first and second relatively parallel beams, and the clip holder assembly comprises a first clip holder, a second clip holder, at least one suture connecting the first clip holder to a first beam of the clip, and at least one suture connecting the second clip holder to a second beam of the clip.

In a second aspect, a system for occluding an anatomical structure is provided which comprises an occlusion clip, a clip holder assembly connected to the occlusion clip by sutures, and a deployment device having shafts that include end effectors adapted to receive the clip holder assembly. The deployment device is adapted to move the occlusion clip to an open position for locating the occlusion clip adjacent an anatomical structure to be occluded, and the deployment device is further adapted to move the occlusion clip to a closed position to permit the occlusion clip to occlude the anatomical structure.

In yet another aspect, a method of deploying a clip for occluding an anatomical structure is provided comprising the steps of locating adjacent the anatomical structure a deployment device having a pair of shafts having distal ends on which a clip holder assembly is installed, wherein a clip for occluding an anatomical structure and having a pair of relatively parallel beam members is connected to the clip holder assembly by sutures, manipulating the deployment device to move the distal ends further apart from each other so as to open the clips moving the beam members of the clip into position adjacent the anatomical structure to be occluded, manipulating the deployment device to move the distal ends closer together so as to allow the clip to occlude the anatomical structure, and cutting the sutures to deploy the clip from the clip holder assembly.

BRIEF DESCRIPTION OF DRAWINGS

The present disclosure includes the following description of certain examples taken in conjunction with the accompanying drawings, in which like reference numerals identify the same elements and in which:

FIG. 4A depicts a perspective view of an example deployment device for use with a clip and clip holder assembly;

FIG. 4B depicts a perspective view of a clip and clip holder assembly for use with the example deployment device of FIG. 4A;

FIG. 4C depicts a perspective view of the example clip and clip holder assembly of FIG. 4B partially installed on the distal ends of the example deployment device of FIG. 4A;

FIG. 4D depicts a perspective view of the example clip and clip holder assembly of FIG. 4B installed on the distal ends of the example deployment device of FIG. 4A;

FIG. 4E depicts a perspective view of the example clip and clip holder assembly of FIG. 4B installed on the example deployment device of FIG. 4A;

FIG. 5A depicts a perspective view of the example deployment device, clip and clip holder assembly of FIG. 4E locating the clip in a closed position above an anatomical structure to be occluded, such as a left atrial appendage;

FIG. 5B depicts a perspective view of the example deployment device, clip and clip holder assembly of FIG. 4E locating the clip in an open position above a left atrial appendage;

FIG. 5C depicts a perspective view of the example deployment device, clip and clip holder assembly of FIG. 4E locating the clip in an open position at the base of a left atrial appendage;

FIG. 5D depicts a perspective view of the example deployment device, clip and clip holder assembly of FIG. 4E locating the clip in a closed position at the base of a left atrial appendage;

FIG. 6A depicts a perspective view of another example clip holder for use with a clip and a deployment device;

FIG. 6B depicts an end view of an example clip and clip holder assembly using a pair of example clip holders of FIG. 6A;

FIG. 6C depicts a cross-sectional side view of an example clip holder of FIG. 6A;

FIG. 6D depicts a cross-sectional side view of the example clip and clip holder assembly of FIG. 6B, in an open position;

FIG. 7 depicts a perspective view of another example clip holder for use with a clip and a deployment device;

FIG. 8A depicts a side view of another example clip holder which includes an alignment indicator and which is partially installed on a distal end of an example deployment device;

FIG. 8B depicts a side view of the example clip holder of FIG. 8A further advanced onto the distal end of the example deployment device;

FIG. 8C depicts an end view of an example clip holder of FIG. 8A;

FIG. 9 depicts a perspective view of another example clip holder for use with a clip and a deployment device;

FIG. 10 depicts a perspective view of another example clip holder for use with a clip and a deployment device;

FIG. 11A depicts a side view of another example clip holder for use with a clip and a deployment device; and FIG. 11B depicts an end view of a clip holder of FIG. 11A installed on a distal end of another example deployment device.

DETAILED DESCRIPTION

Figure 1:
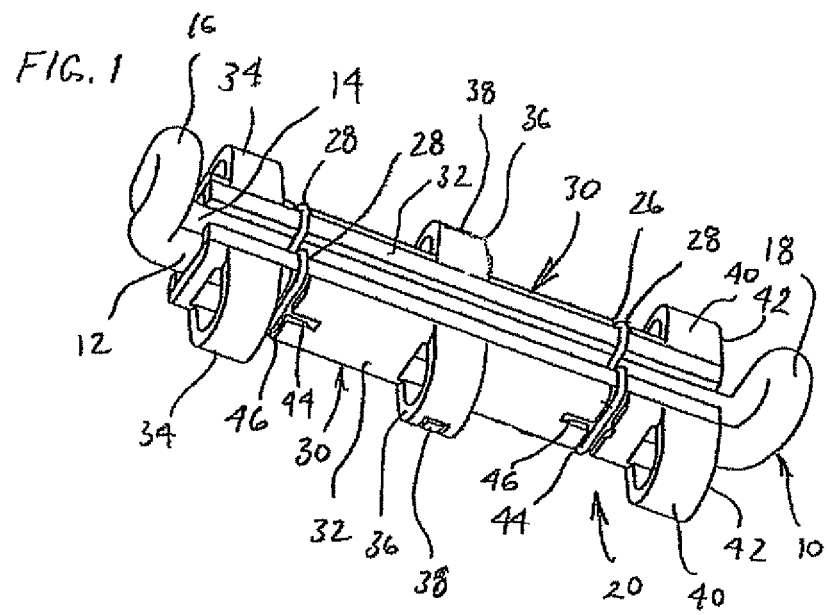
FIG. 1 depicts a perspective view of an example clip and clip holder assembly to be used for occluding an anatomical structure, with the clip shown in a simplified form.

Although the following discloses example apparatus and methods for use in occluding anatomical structures, it will be understood by one of ordinary skill in the art that the teachings of this disclosure are in no way limited to the examples shown. On the contrary, it is contemplated that the teachings of this disclosure may be implemented in alternative configurations and environments. For example, although the example apparatus described herein is described in conjunction with a configuration for use with a clip to occlude an LAA, those of ordinary skill in the art will readily recognize that the example apparatus and methods may be used with alternative clips, and/or to occlude other anatomical structures and may be configured to correspond to such other structures as needed. Accordingly, while the following describes an example apparatus and methods of use thereof persons of ordinary skill in the art will appreciate that the disclosed examples are not the only way to implement such apparatus and/or methods, and the drawings and descriptions should be regarded as illustrative in nature and not restrictive.

It will be appreciated that the example of an apparatus for deploying a clip may be used with a clip that is intended to act as a clamp. Moreover, the clip may take many forms, but preferably includes relatively parallel beam members which are utilized to apply a clamping force. Examples of such clips are illustrated herein, as well as are shown and described in reference to FIG. 44 of U.S. patent application Ser. No. 12/033,935 and in U.S. Provisional Patent Application Ser. No. 61/082,266, both of which are incorporated herein by reference.

Clips having relatively parallel beam members, as will be disclosed in greater detail below, may be deployed in a position secured to an anatomical structure. To the extent that such an anatomical structure would otherwise permit communication of fluid through the anatomical structure, the clamping or other engagement of the clip on the anatomical structure may substantially prevent the communication of fluid through, into, or out of the anatomical structure. The following example of a clip may therefore be used to form an occlusion in the anatomical structure. It will be appreciated, however, that a clip need not necessarily be used to form a complete occlusion in an anatomical structure, and may be instead used simply to restrict or regulate the flow of fluid through, into, or out of an anatomical structure.

In addition, it will be appreciated that the following examples of an apparatus for deploying a clip may be configured such that it is atraumatic with regard to the anatomical structure being occluded, adjacent organs, and/or adjacent tissue. Due to the varying dimensions of the LAA and other anatomical structures between individuals, it will be appreciated that the overall dimensions or configurations of such an apparatus may be varied to accommodate anatomical structures of different dimensions or for other purposes.

The examples of apparatus for deploying a clip may accommodate a clip that includes a sock or retention material configured to enshroud at least some portion of the components of the clip. A sock may comprise a knit, braided polyester material. Of course, any other suitable materials may be used for a sock, including but not limited to polyethylene. It also will be appreciated that a sock is optional and may be configured to provide friction and to facilitate the growth of scar tissue to hold the clip adjacent the anatomical structure. A sock may also be sutured to tissue to further secure a clip in place. At least one manner in which a sock may be incorporated in the example clip and associated methods is described in more detail below. However, it will become apparent to those of ordinary skill in the art that components of a clip may be provided with a coating, textured or perforated surface, or some other configuration may be used to provide retention results similar to those provided by a sock. As one example, ionic plasma deposition (IPD), such as is available from Chameleon Scientific of Plymouth Minn., may be employed to create a surface-engineered nanostructure coating on components to enhance adhesion and scar tissue growth. Molecular plasma deposition of colloidal materials onto metal or nonmetal surfaces to affect biological activity also is discussed in U.S. Pat. No. 7,250,195, incorporated herein by reference.

Turning to the drawings, FIGS. 1-11B illustrate various views of clips, clip holders and/or portions of deployment devices. For instance, FIG. 1 illustrates an example clip 10 held by an example clip holder assembly 20. The clip 10 is shown in a simplified view, with a continuous covering or coating. The example clip 10 is shown in a configuration having a first beam 12, an opposed second beam 14, with the first and second beams 12, 14 connected at a first end 16 and at a second end 18. Each end 16, 18 is configured as a partial loop, with the ends biasing the beams 12, 14 toward a closed position wherein the beams are adjacent each other.

The example clip holder assembly 20 includes first and second clip holders 30, and a pair of sutures 50. The example clip holders are preferably made from Gamma stabilized polycarbonate and are radiopaque, although it will be appreciated that they may be made from suitable alternative materials having different features as desired. The example clip holders 30 are intended to be non-implantable, and provide the interface between the implantable example clip 10 and a deployment tool, as discussed in greater detail herein. Each example clip holder 30 has a body portion 32 generally in the shape of a channel that receives a beam portion of a clip, and three upstanding members, in the form of raised stirrups, extending from the rear side of the channel. The first upstanding member or stirrup 34 is a loop configured with a passageway therethrough to accept a deployment device, as will be discussed in greater detail herein. The second stirrup 36 is a similarly configured loop but includes a biasing finger 38 which will apply a gripping force to a deployment device, as will be discussed herein. The third stirrup 40 is configured as a loop of similar size to the first and second loops, but is closed at the distal end by a wall 42, which will act as a stop when inserting a deployment device.

The body portion 32 also includes on the rear side of the channel a pair of lateral slots 44. Each of the lateral slots 44 is perpendicularly intersected by a secondary small, ramped slot 46. The pair of example clip holders 30 may be connected to the respective first and second beams 12, 14 of the example clip 10 by use of sutures 50. The sutures 50 preferably are made from biocompatible polyester, such as Poly (ethylene terephthalate), or suitable alternative materials that permit them to be implantable. Each suture 50 is located in one of the lateral slots 44 and connects the respective beam 12, 14 to a clip holder 30 by forming a knot in each suture. In turn, the example clip 10 may be released from the example clip holder assembly 20 by cuffing the sutures 50 at any point along their length. If the deployment device has been removed from the clip holder assembly 20 prior to release of the clip holder assembly from the clip, then the secondary slots 46 provide a convenient location at which a cutting device may be used to reach beneath and cut a respective suture 50. The clip holders 30 then may be removed from the patient. Also, in the event the sutures 50 are not made of implantable materials, then the sutures 50 must be removed after being cut to deploy the clip 10. If the sutures 50 are made of implantable materials, then they may be left in the patient, or removed during the clip deployment procedure.

Figure 2:
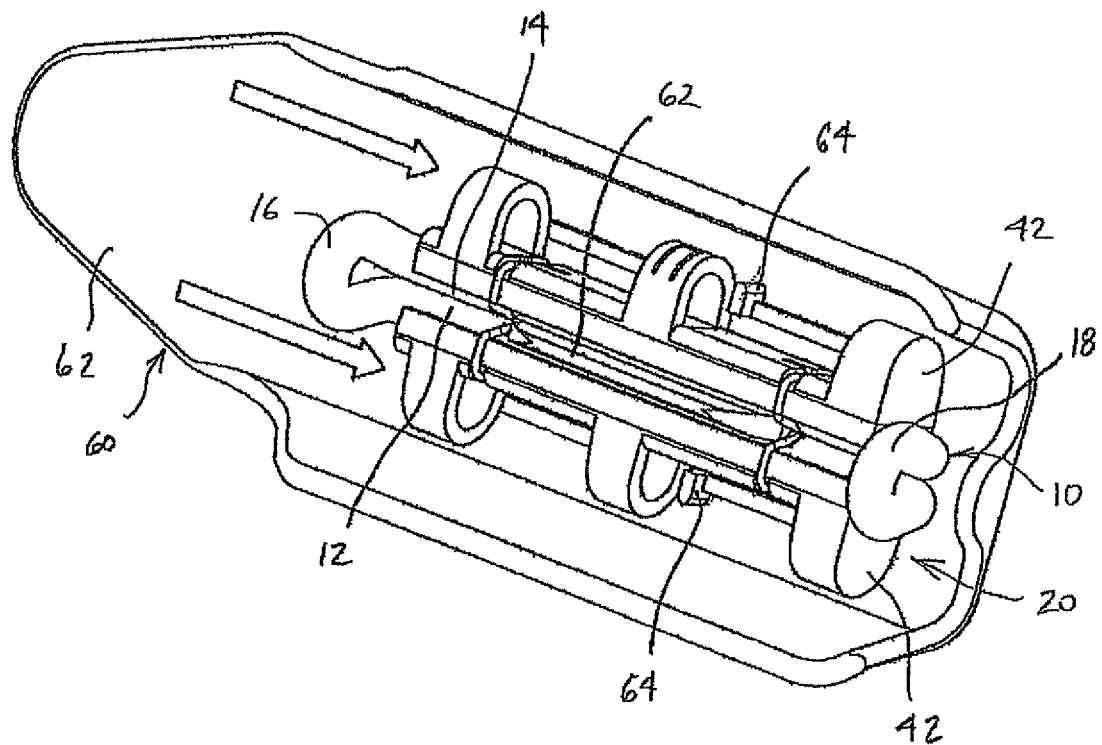
FIG. 2 depicts the example clip and clip holder assembly of FIG. 1 positioned in a loading aid.

In FIG. 2, an example clip 10 and clip holder assembly 20 are positioned in a loading aid 60. Loading aid 60 is preferably made from a polymeric or other suitable material, and includes an outer shell 62, an upstanding central rib 64, and upstanding stops 66. A clip 10 connected to a clip holder assembly 20 may be installed in the loading aid 60 by pressing the clip 10 toward the outer shell 62, so as to part the beams 12, 14 and force them to be positioned adjacent the central rib 64. Preferably, care should be taken to simultaneously locate the clip holder assembly 20 so as to have a portion abut at least one upstanding stop 66. Installing the clip 10 and clip holder assembly 20 in the loading aid 60 provides a ready means for packaging the components and for convenient handling when installing the clip 10 and clip holder assembly 20 on a respective deployment device.

Figure 3A:
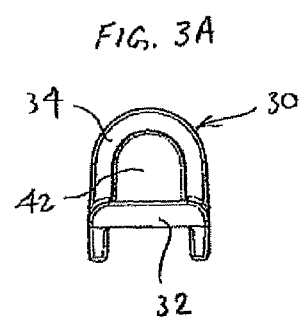
FIG. 3A depicts an end view of a clip holder of the example clip holder assembly of FIG. 1.

Turning to FIGS. 3A-3E, the structure of the example clip holder 30 is shown in greater detail. In FIG. 3A, the example clip holder 30 is shown in an end view, from the end proximate the first stirrup 34. In this view, the generally channel-shaped body portion 32 is facing downward and may accept a beam of an example clip 10. The upstanding members or stirrups 34, 36 and 40 extend upward, and the wall 42 is viewable through the passageways through the respective stirrups.

Figure 3B:
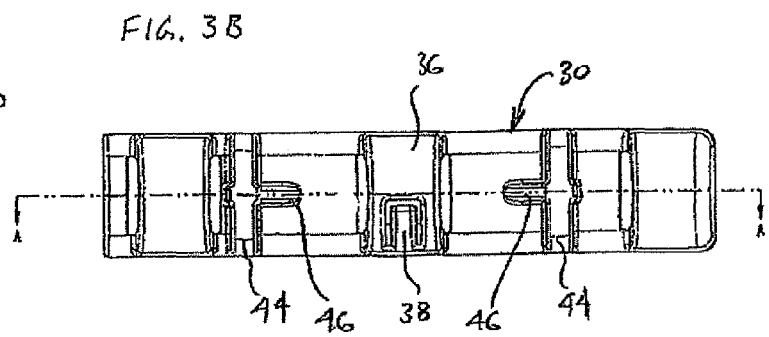
FIG. 3B depicts a top view of a clip holder of the example clip holder assembly of FIG. 1.
Figure 3C:
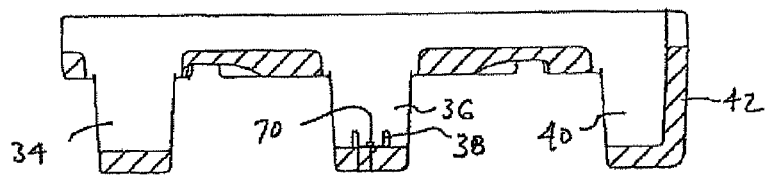
FIG. 3C depicts an inverted cross-sectional side view of a clip holder of the example clip holder assembly of FIG. 1, taken at line A-A in FIG. 3B.
Figure 3E:
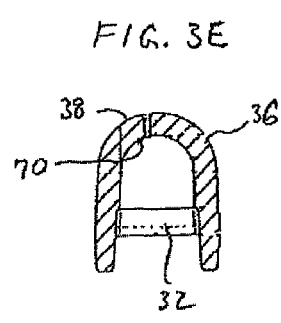
FIG. 3E depicts a cross-sectional end view of a clip holder of the example clip holder assembly of FIG. 1, taken at line D-D in FIG. 3D.
Figure 3D:
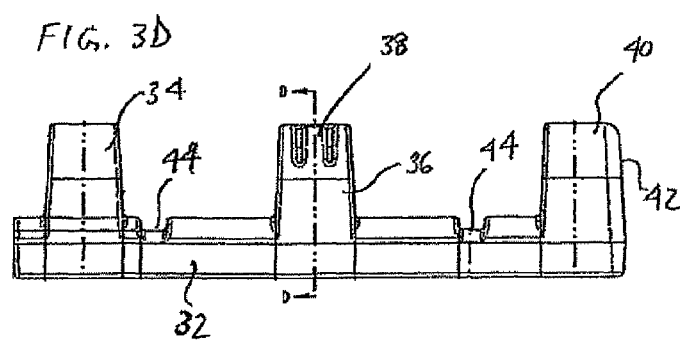
FIG. 3D depicts a side view of a clip holder of the example clip holder assembly of FIG. 1.

A top view of the example clip holder 30 is shown in FIG. 3B while a side view is shown in FIG. 3D. These views show the location of the lateral slots 44, with FIG. 3B showing the location of the intersecting secondary slots 46 in the body portion 32. These views also illustrate the biasing finger 38 in the second stirrup 36. The cross-sectional view of FIG. 3C, taken along the section line A-A in FIG. 3B, illustrates the underside of the biasing finger 38, and the wall 42 at the distal end of the third stirrup 40. The underside of the biasing finger 38 includes a protrusion 70, which also is shown in FIG. 3E in a cross-sectional view taken along the section line D-D in FIG. 3D. As best seen in the cross-sectional views in FIGS. 3C and 3E, when the biasing finger 38 is in a relaxed position, it will slightly interfere with the passageway otherwise defined by the stirrups 32, 36 and 40. Thus, when installed on a deployment device, engagement with the protrusion 70 will cause the biasing finger 38 to bend, thereby applying a gripping force to the deployment device at the protrusion 70.

With the disclosure of various example clip holders herein, and the disclosure relating to the example deployment devices, it will be appreciated that clip holders may include any number of stirrups, and any number of biasing fingers or no biasing finger at all. Indeed, the deployment device itself will tend to exert some retention preload on the clip holders as a result of a tool spring. Thus, a preset retention force may be selected based on various configurations which tend to increase or decrease the force required to install or remove the clip holders from the deployment device. If desired, it also is possible to employ a detent configuration use detents wherein a protrusion on a clip holder engages a recess or stop on a deployment device, or vice versa.

FIGS. 4A-4E illustrate an example deployment device 80, and the positioning of the example clip 10 and clip holder assembly 20 on the deployment device 80. In FIG. 4A, the example deployment device 80 is shown having two shafts 82, 84, pivotally connected at a hinge 86. The hinged shafts 82, 84 may be made from AISI 420 stainless steel or biocompatible polymeric relatively rigid materials, in a sterilized single use format, or in a reusable, non-sterilized format that requires sterilization prior to use. At a proximal end of the hinged shafts 82, 84 are respective finger rings 82a, 84a, which accommodate two fingers of a user. For improved comfort and handling, the finger rings 82a, 84a may include a suitable placiticized or rubberized coating. At a distal end of the hinged shafts 82, 84 are respective end effectors 82b, 84b, each in a generally cylindrical rod shape.

As seen in FIGS. 4A and 4E, toward the proximal end of the deployment device 80, a stop 88 is fixed to hinged shaft 82. The stop 88 is located so as to cause the opposed hinged shaft 84 to engage the stop 88 when the finger rings 82a, 84a are moved toward each other. It will be appreciated that the location and length of the stop 88 may be selected to limit the maximum displacement and distance between the end effectors 82b, 84b of shafts 82, 84 when the deployment device 80 is in a fully opened position. When in a relaxed position, a biasing member 90, located between the hinged shafts 82, 84, tends to force the finger rings 82a, 84a toward a spaced apart position. This causes the end effectors 82b, 84b to be moved toward each other to a preselected distance apart which is associated with a closed position.

An example clip 10 and example clip holder assembly 20 are illustrated in FIG. 4B. The same numbering is used as with the preceding drawings, with the covering on the clip 10 being shown in the form of a mesh fabric material, or sock. FIG. 4B is an upper perspective view from an end by which one can see through the passageways through the upstanding members or stirrups in the respective example clip holders 30. In FIG. 4C, the example clip 10 and clip holder assembly 20 is shown in a position where it is partially installed on the respective shafts 82, 84 at the end effectors 82b, 84b of an example deployment device 80. In the position shown, the end effectors 82b, 84b have passed through the first stirrups 34, but have not yet reached the second stirrups 36.

In FIGS. 4D and 4E, the example clip 10 and clip holder assembly 20 are shown in a further position of installation on the example deployment device 80. The end effectors 82b, 84b have been inserted through the stirrups 34, 36 and 40 until reaching the wall 42 in the distal end of the third stirrup 40. In this position, the clip 10 and clip holder assembly 20 are fully installed on the deployment device 80 and ready for use. It will be appreciated that the loading aid 60, illustrated in FIG. 2, may be used to package and/or facilitate holding of the example clip 10 and example clip holder assembly 20 when attempting to insert the end effectors 82b, 84b of the example deployment device 80.

By disclosure of the various example clip holder assemblies herein, it will become apparent to one of ordinary skill in the art that any number of biasing fingers may be used, from 0 to 1 or more. Indeed, when installed on a deployment device, the end effectors will tend to exert a preload on the beams of the clip which will increase the force needed to remove the clip from the deployment device. It also will be appreciated that other configurations of protrusions and/or biasing fingers or elements may be utilized to provide a gripping force which tends to resist the removal of the clip holders from the deployment device.

It also will be appreciated that in any of the examples disclosed herein, regardless of the positioning of the clip holders relative to the respective beams of the clip, the deployment device may include various angular relationships along the length of its shafts. Thus, the deployment shafts may include bends along the shafts to accommodate specific orientations of the clip relative to the anatomical structure and desired egress.

With the example clip 10 and example clip holder assembly 20 installed on an example deployment device 80, the user is ready to position the apparatus for deployment of the clip 10. FIGS. 5A-5D are a series of perspective views illustrating the positioning of the apparatus prior to deployment of the example clip 10. In these figures, the apparatus is shown with an example clip 10 connected to an example clip holder assembly 20, as illustrated in the prior drawings. These elements are further shown installed on an example deployment device 80, as illustrated in the prior drawings. In FIG. 5A, the apparatus is shown with the example clip 10 and the example deployment device 80 in a closed position and located above an anatomical structure to be occluded, which in this instance is an LAA 96 on a heart 98. In FIG. 5B, the end effectors 82b, 84b and the clip 10 have been moved to a fully open position, by squeezing the finger rings 82a, 84b toward each other. With the example clip 10 in the fully open position, the LAA 96 is visable through the clip 10, between the beams 12, 14.

In FIG. 5C, the example clip 10 is in a fully open position and has been moved to the base of the LAA 96, into a potential location for occluding the LAA 96. Given the connection between the example clip 10 and the example clip holder assembly 20, the user is permitted to open and close the clip 10, as needed, to achieve an appropriate placement of the example clip 10 for the desired occlusion purpose. In FIG. 5D, the clip 10 is shown at the base of the LAA 96, in a closed position. If the user is satisfied with this positioning of the clip 10, then as discussed above, the user may proceed to cut the sutures 50 to release and deploy the clip 10. It will be appreciated that, depending on the material of the sutures 50, the sutures 50 may be left in the patient, or removed, as needed. Further, it will be appreciated that, after deploying the clip 10, the clip holders 30 of the clip holder assembly 20 may remain on the deployment device 80 for easy removal from the patient with the deployment device 80. Alternatively, the deployment device 80 may be removed from the clip holders 30, permitting the user to observe the effectiveness of the clip 10 apart from the influence of the deployment device 80 prior to releasing the clip 10 from the clip holders 30. In such an instance, if needed, the end effectors 82b, 84b of the deployment device 80 may be reinserted into the stirrups 34, 36 and/or 40 to reposition or remove the clip 10. Also, if the end effectors 82b, 84b have been removed from the clip holders 30 of the clip holder assembly 20 and the clip is determined to be in an appropriate location, then the deployment device 80 and the clip holders 30 may be independently removed from the patient.

Turning to FIGS. 6A-6D, another example clip 110 is shown with an example clip holder assembly 120. As best seen in the cross-sectional view of FIG. 6D, the example clip 110 is shown in a configuration having a first beam 112, an opposed second beam 14, with the first and second beams 112, 114 being hollow and connected via an elongated suture 115 that is threaded through both beams in a slip arrangement at a first end 116 and gathered for tying into a know at a second end 118. It will be appreciated that as the two ends of the suture 115 are drawn together and the suture 115 is increasing drawn tight, the beams 112, 114, will be drawn together and will apply a clamping force to any structure located therebetween.

As illustrated in the perspective view 6A and the cross-sectional views 6C and 6D, the example clip holder assembly 120 includes first and second clip holders 130, and a pair of sutures 150. The example clip holders are preferably made from similar materials to those described above with respect to example clip holders 30. Each example clip holder 130 has a body portion 132 generally in the shape of a channel having ends 134, 136. The channel-shape of the body 132 includes a top portion 138 and side walls 140 depending therefrom, and effectively forms a single elongated stirrup for engagement with a deployment device. The ends 134, 136 include apertures to accept end effectors of a deployment device. In this example, the apertures are oblong, which additionally serves to prevent the clip holders 130 from rotating on correspondingly shaped end effectors of a deployment device (not shown).

The top portion 138 includes a pair of lateral slots 144. The pair of example clip holders 130 may be connected to the respective first and second beams 112, 114 of the example clip 110 by use of sutures 150. The sutures 150 preferably are made from materials similar to those discussed above with respect to sutures 50. Each suture 150 is located in one of the lateral slots 144 and connects the respective beam 112, 114 to a clip holder 130 by forming a knot in the suture. In turn, the example clip 110 may be released from the example clip holder assembly 120 by cutting the sutures 150. As discussed above with respect to the sutures 50, the sutures 150 may be left in the patient, or alternatively retrieved during the clip deployment procedure.

Turning to FIG. 7, another example clip holder 230 is illustrated. This example clip holder 230 is somewhat similar to the example clip holder 30 discussed above, but notably includes a biasing finger 238 on each of three like stirrups. Indeed, it will be appreciated that any number of stirrups may be used, and each stirrup may or may not include a biasing finger, as desired. Thus, a pair of clip holders 230, and a pair of sutures 250 would be provided. The example clip holders 230 may be made of similar materials to those discussed above with respect to example clip holder 30.

In the example illustrated in FIG. 7, the example clip holder 230 has a body portion 232 generally in the shape of a channel, with three raised stirrups 234 extending from the rear side of the channel. The three stirrups 234 are configured as a loop with a passageway therethrough to accept a deployment device. None of the stirrups 234 have a closed end wall. Rather, with this example clip holder 230, an end effector 82b, 84b of a deployment device may be inserted through the stirrups 234 until a shaft 82, 84 engages a stirrup 234, serving as the stop for the fully installed position. As noted above, the three stirrups 234 of the example clip holder 230 each include a biasing finger 238 which is configured similar to the biasing finger 38 discussed above with respect to example clip holders 30. Thus, there is much design discretion with respect to the level of gripping force that a clip holder may apply to a deployment device.

In the example clip holder 230 shown in FIG. 7, the body portion 232 includes on the rear side of the channel a pair of lateral slots 244. A pair of example clip holders 230 may be connected to respective first and second beams of an example clip, such as beams 12, 14 of example clip 10, by use of sutures 50 (not shown). As discussed above, the sutures 50 may be made of suitable materials and the connection of the example clip holders 230 to an example clip 10 may be established by forming a knot in each suture. The example clip 10 may be released from the example clip holder assembly 220 by cutting the sutures 50.

FIGS. 8A-8C illustrate a modification to the above-described example clip holder 30. In this example, the clip holder 330 includes an alignment indicator, to help ensure that the clip holder 330 has been properly installed on a respective deployment device. As shown in FIGS. 8A-8C, an alignment indicator is formed using a slidable member 372 that is received in a passage 374 in the body 332 of the clip holder 330. The clip holder 330 is in all other respects identical to the previously described clip holder 30.

As best seen in FIG. 8A, the alignment indicator is positioned so as to extend outward from the body portion 332 of the clip holder 330 prior to installation on a deployment device. If the clip holder 330 is improperly positioned with respect to the deployment device, such as being inverted relative to its proper position, the slidable member 372 of the alignment indicator will not engage the respective shaft 82, 84 of the deployment device while being installed on a respective end effector 82b, 84b. Thus, the slidable member would remain in a position extending outward from the clip holder 330 and beyond the respective shaft 82, 84, indicating that the clip holder 330 had been improperly installed.

As seen in the transition from FIG. 8A to FIG. 8B, when properly aligned on the respective end effector 82b, 84b, the slidable member 372 will engage the respective shaft 82, 84 and be pushed inward within the passage 374 in the body portion 332 of the clip holder 330 and further concealed, as the clip holder 330 is more fully installed on the deployment device. In such a properly aligned position, the slidable member 372 would not extend outward and obstruct normal usage of the clip holder 330, thus indicating that the clip holder 330 has been properly installed.

Another example clip holder 430 is illustrated in FIG. 9. The example clip holder 430 may similarly be used in pairs and with sutures 50 in a clip holder assembly 420 (not shown) to deploy clips, such as above-disclosed example clip 10. Example clip holder 430 preferably is made of similar materials to those of example clip holder 30, and includes a body portion 432 generally in the shape of a channel. The body 432 has a single raised stirrup 434 extending from the rear side of the channel, and having a biasing finger 436. Extending from a portion of a side wall of the stirrup 434 is a reinforcing rib 438 that extends along the length of the body portion 432 of the example clip holder 430. The reinforcing rib 438 includes a projection 440 formed as a stop proximate the distal end of the rib 438. The body portion 432 also includes slots 444 for locating sutures 50 as described above with respect to the other examples. The reinforcing rib 438 permits the clip holder to use fewer stirrups and to potentially be shorter in length relative to an example clip holder 30 for use with a clip 10 of the same length.

Yet another example clip holder 530 is illustrated in FIG. 10. The example clip holder 530 also may be used in pairs and with sutures 50 in a clip holder assembly 520 (not shown) to deploy clips, such as above-disclosed example clip 10. Example clip holder 530 preferably is made of similar materials to those of example clip holder 30, and includes a body portion 532 generally in the shape of a channel. The body 532 has a central raised stirrup 534 extending from the rear side of the channel and having a biasing finger 536. The side walls of the stirrup 534 broaden toward their base where they join the body portion 532. The broadened side walls of the stirrup 534 extend along a substantial portion of the length of the body portion 532 in a reinforcing manner, much as is provided in reinforcing rib 438 of the above-disclosed example clip holder 430. The clip holder 530 also includes a projection 538 on the body portion 532 as a stop to locate a respective end effector of a deployment device in a fully installed position. The body portion 532 also includes slots 544 for locating sutures 50 as described above with respect to the other examples. As with the example shown in FIG. 9, the broadened stirrup 534 of the example clip holder 530 shown in FIG. 10 permits the clip holder 530 to use fewer stirrups and to potentially be shorter in length relative to an example clip holder 30 for use with a clip 10 of the same length.

Turning to FIGS. 11A and 11B, another example clip holder 630 is disclosed for use with clips, such as above-disclosed example clip 10. The example clip holder 630 may be used in pairs and with sutures 50 in a clip holder assembly 620 (not shown). The example clip holders 630 are preferably made from similar materials to those disclosed for use in the above-disclosed examples. Each example clip holder 630 has a body portion 632 generally in the shape of a downward extending channel, with a pair of arms 634 extending further downward from the channel, and having tapered ends 636. The body portion 632 also includes a pair of raised stirrups 638 extending from the rear side of the channel. The stirrups 638 are loops configured with passageways therethrough to accept ends of a deployment device. A projection 642 is located on the body portion 632 and provides a stop for engagement with an end of a deployment device. The body portion 632 further includes a lateral slot 644 for locating a suture 50 to connect the example clip holder 630 to an example clip 10.

As best seen in FIG. 11B, the stirrups 638 generally have rectangular-shaped openings and passageways therethrough to accept correspondingly shaped end effectors 682b, 684b of an example deployment device 680. Clip holders 630 are intended to be located above the beams of an example clip 10, as opposed to adjacent the outer side surfaces of the beams. Thus, the arms 634 of clip holders 630 extend between the beams of a clip 10 and are used to push the beams apart from each other to open the clip, as opposed to pulling on the beams to open the clip 10, as required with the example clip holders 30. Given the torque created by the arms 634, the stirrup to end effector engagement must resist rotation about the longitudinal axis of the end effector. This is provided by use of the generally rectangularly shaped openings in the stirrups 638 and the corresponding generally rectangular end effectors 682b, 684b.

This alternative orientation of the clip holders 630 above the clip beams, as opposed to being positioned laterally outside of the clip beams, may be beneficial in tight locations that require a narrower assembly. The deployment device 680 (not shown) may be structured similarly to deployment device 80, but with end effectors having a generally rectangular or oblong cross-section to prevent rotation of the clip holders on the end effectors, as indicated with end effector 682b at the end of the shaft 682, shown in FIG. 11B. Use of this clip holders 630 also permit the end effectors to be spaced more closely together when in the closed position relative to the other examples having the clip holders located laterally outside of the clip beams.

Having shown and described an example embodiment, further adaptations of the methods, components and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, steps, and the like discussed above are illustrative and are not necessarily required. Accordingly, the scope of the present invention should be considered in terms of the following claims and is understood not to be limited to the details of structure and operation shown and described in the specification and drawings.

The invention claimed is:

1. A clip holder assembly for use in deploying a clip adapted to occlude an anatomical structure comprising: a first clip holder; a second clip holder; at least one suture connecting the first clip holder to a first beam of the clip; at least one suture connecting the second clip holder to a second beam of the clip; wherein the first clip holder and the second clip holder are adapted to dismount from a clip deployment tool after deployment of the clip; and wherein each of the first and second clip holders includes a body having a channel portion adapted to receive the respective beam of the clip.

2. The assembly of claim 1, wherein each of the first and second clip holders includes at least one upstanding member adapted to engage the deployment device.

3. The assembly of claim 2, wherein each of the upstanding members includes a reinforcing rib extending a substantial portion of a length of the respective clip holder.

4. The assembly of claim 2, wherein each of the upstanding members has a length and each of the clip holders has a length and the length of each upstanding member is less than the length of each clip holder.

5. The assembly of claim 2, wherein each of the upstanding members is configured to have a broadened base that extends along sides of the respective clip holder.

6. The assembly of claim 2, wherein each of the first and second clip holders includes at least three upstanding members adapted to engage the deployment device.

7. The assembly of claim 2, wherein at least one of the upstanding members on either the first clip holder or the second clip holder includes a biasing finger adapted to engage the deployment device.

8. The assembly of claim 7, wherein each of the upstanding members on at least one of the first or the second clip holders includes a biasing finger adapted to engage the deployment device.

9. The assembly of claim 2, wherein each of the upstanding members on either the first clip holder or the second clip holder is adapted to slidably receive a shaft of the deployment device.

10. The assembly of claim 9, wherein the shaft of the deployment device is cylindrical.

11. The assembly of claim 9, wherein the shaft of the deployment device is not cylindrical.

12. A method of deploying a clip for occluding an anatomical structure comprising:
    locating adjacent an anatomical structure a deployment device mounted to a clip holder, wherein a clip for occluding the anatomical structure includes a pair of relatively parallel, linear beams connected to the clip holder by at least one suture;
    manipulating the deployment device to open the clip, where manipulation of the deployment device does not change the orientation of the clip holder with respect to the deployment device;
    moving the clip into position adjacent the anatomical structure to be occluded;
    manipulating the deployment device to allow the clip to occlude the anatomical structure; and,
    cutting the at least one suture to release the clip from the clip holder.

13. The method of deploying a clip of claim 12, further installing a clip and clip holder assembly on the shafts of the deployment device prior to locating the clip and clip holder assembly adjacent the anatomical structure.

14. A method of preparing an occlusion clip for deployment within an anatomical structure, the method comprising:
    mounting a clip holder to an occlusion clip using at least one suture to form a clip holder assembly; and,
    mounting, after forming the clip holder assembly, the clip holder assembly to a deployment tool;
    wherein the deployment tool is operative to reposition the occlusion clip between a closed position and an open position.

15. A method of deploying a clip for occluding an anatomical structure comprising:
    connecting a first clip holder to an occlusion clip using a first suture, the occlusion clip comprising a pair of relatively parallel, linear beams;
    connecting a second clip holder to the occlusion clip using a second suture;
    mounting a deployment device to the first and second clip holders;
    manipulating the deployment device to open the occlusion clip;
    moving the occlusion clip into position adjacent an anatomical structure to be occluded;
    manipulating the deployment device to allow the occlusion clip to occlude the anatomical structure;
    removing the deployment device; and,
    cutting the first and second sutures to release the clip from the first and second clip holders.

* * * * *